(12) United States Patent
Kosco-Vilbois et al.

(10) Patent No.: US 8,734,790 B2
(45) Date of Patent: May 27, 2014

(54) ANTI-TLR4 ANTIBODIES AND METHODS OF USE THEREOF

(75) Inventors: Marie Kosco-Vilbois, Minzier (FR); Katrien L. De Graaf, Nyon (CH); Thierry Berney, Arenthon (FR); Laurianne Santa Giovannoni, Annemasse (FR); Domenic Bosco, Geneva (CH)

(73) Assignee: Novimmune SA, Geneva (CH)

( * ) Notice: Subject to any disclaimer, the term of this patent is extended or adjusted under 35 U.S.C. 154(b) by 0 days.

(21) Appl. No.: 13/346,911

(22) Filed: Jan. 10, 2012

(65) Prior Publication Data

US 2012/0177648 A1   Jul. 12, 2012

Related U.S. Application Data

(60) Provisional application No. 61/431,191, filed on Jan. 10, 2011.

(51) Int. Cl.
| | | |
|---|---|---|
| *A61K 39/395* | (2006.01) | |
| *A61P 37/06* | (2006.01) | |
| *C07K 16/28* | (2006.01) | |

(52) U.S. Cl.
USPC ............. 424/130.1; 424/134.1; 424/133.1; 424/135.1; 424/139.1; 424/141.1; 424/143.1; 530/387.1; 530/388.1; 530/388.22

(58) Field of Classification Search
None
See application file for complete search history.

(56) References Cited

U.S. PATENT DOCUMENTS

| | | | | |
|---|---|---|---|---|
| 5,688,824 | A | * | 11/1997 | Williams .................... 514/378 |
| 7,312,320 | B2 | | 12/2007 | Elson et al. |
| 7,592,003 | B2 | | 9/2009 | Nagai et al. |
| 7,674,884 | B2 | | 3/2010 | Elson et al. |
| 8,546,539 | B2 | | 10/2013 | Elson et al. |

FOREIGN PATENT DOCUMENTS

| | | | |
|---|---|---|---|
| WO | WO2009/101479 | * | 8/2009 |

OTHER PUBLICATIONS

Alegre et al, transplantation, 2008, vol. 86, pp. 1-9.*
Goldberg et al, (FASEB J. 2007, vol. 21, pp. 2840-2848.*
Dunn-Siegrist et al, Journal of Biological Chemistry, 2007, vol. 282, No. 48, pp. 34817-34827.*

* cited by examiner

*Primary Examiner* — Bridget E Bunner
*Assistant Examiner* — Fozia Hamud

(57) ABSTRACT

This invention relates generally to antibodies that specifically bind Toll-like Receptor 4 (TLR-4), and to methods of using the anti-TLR4 antibodies as therapeutics and to methods of using the anti-TLR4 antibodies in methods of preventing transplant rejection and/or prolonging survival of transplanted biological material.

13 Claims, 4 Drawing Sheets

ANTI-TLR4 ANTIBODIES AND METHODS OF USE THEREOF

RELATED APPLICATIONS

This application claims the benefit of and priority to U.S. Provisional Patent Application No. 61/431,191, filed Jan. 10, 2011, which is herein incorporated by reference in its entirety.

FIELD OF THE INVENTION

This invention relates generally to antibodies that specifically bind Toll-like Receptor 4 (TLR-4), and to methods of using the anti-TLR4 antibodies as therapeutics and to methods of using the anti-TLR4 antibodies in methods of preventing transplant rejection and/or prolonging survival of transplanted biological material.

INCORPORATION-BY-REFERENCE OF SEQUENCE LISTING

The contents of the text file named "424001USSeqList.txt," which was created on Jan. 9, 2011 and is 41.7 KB in size, are hereby incorporated by reference in their entirety.

BACKGROUND OF THE INVENTION

Organ and tissue transplantation is the preferred clinical approach to treat patients suffering from organ failure or complications arising from diseases of specific organs and tissues. However, transplant patients face a lifetime of immunosuppressive therapy and the risk of losing the new organ due to rejection. Although improvements have been made in the transplantation process, rejection remains the most common complication following transplantation and is the major source of morbidity and mortality. Transplant rejection occurs when the immune system of the recipient of a transplant attacks the transplanted organ or tissue. Rejection is an adaptive immune response and is mediated through both T lymphocyte-mediated and humoral immune mechanisms.

Thus, there remains a need for methods to promote organ or tissue transplantation tolerance in patients.

SUMMARY OF THE INVENTION

The invention provides methods of inhibiting rejection of and/or prolonging survival of transplanted biological material in a subject using antibodies that specifically bind Toll-like receptor 4 (TLR4).

The invention provides methods of inhibiting rejection of and/or prolonging survival of transplanted biological material in a subject by contacting the biological material to be transplanted with an antibody or immunologically active fragment thereof that specifically binds a Toll-like receptor 4 (TLR4) polypeptide to produce a transplantable composition, and implanting the transplantable composition at a desired location in the subject.

In some embodiments, the methods also include the step of administering to the subject who has been implanted with the biological material one or more additional doses of an antibody or immunologically active fragment thereof that specifically binds TLR4, wherein the antibody is administered in an amount sufficient to prevent transplant rejection or prolong survival of the transplanted biological material in the subject. The additional dose of anti-TLR4 antibody can be administered during the transplant, after the transplant or both.

The invention provides methods of inhibiting rejection of or prolonging survival of transplanted biological material in a subject by contacting the biological material to be transplanted with an antibody or immunologically active fragment thereof that specifically binds a Toll-like receptor 4 (TLR4) polypeptide to produce a transplantable composition, implanting the transplantable composition at a desired location in the subject, and administering to the subject one or more additional doses of an antibody or immunologically active fragment thereof that specifically binds TLR4, wherein the antibody is administered in an amount sufficient to prevent transplant rejection or prolong survival of the transplanted biological material in the subject. The additional dose of anti-TLR4 antibody can be administered during the transplant, after the transplant or both.

The invention also provides methods of treating a subject who has received or will receive a transplant of biological material by administering to the subject one or more doses of an antibody or immunologically active fragment thereof that specifically binds a Toll-like receptor 4 (TLR4) polypeptide, wherein the antibody is administered in an amount sufficient to prevent transplant rejection or prolong survival of the transplanted biological material in the subject.

In some embodiments, the subject is a mammal. In a preferred embodiment, the subject is a human.

In some embodiments, the TLR4 polypeptide is a human TLR4 polypeptide. In some embodiments, the human TLR4 polypeptide comprises the amino acid sequence:

```
                                                           (SEQ ID NO: 11)
  1 mmsasrlagt lipamaflsc vrpeswepcv evvpnityqc melnfykipd nlpfstknld 61 lsfnplrhlg sysffsfpel qvldlsrcei qtiedgayqs lshlstlilt gnpiqslalg 121 afsglsslqk lvavetnlas lenfpighlk tlkelnvahn liqsfklpey fsnltnlehl 181 dlssnkiqsi yctdlrvlhq mpllnlsldl slnpmnfiqp gafkeirlhk ltlrnnfdsl 241 nvmktciqgl aglevhrlvl gefrnegnle kfdksalegl cnltieefrl ayldyylddi 301 idlfncltnv ssfslvsvti ervkdfsynf gwqhlelvnc kfgqfptlkl kslkrltfts 361 nkggnafsev dlpslefldl srnglsfkgc csqsdfgtts lkyldlsfng vitmssnflg 421 leqlehldfq hsnlkqmsef svflslrnli yldishthtr vafngifngl sslevlkmag 481 nsfqenflpd iftelrnltf ldlsqcqleq lsptafnsls slqvlnmshn nffsldtfpy
```

```
541 kclnslqvld yslnhimtsk kqelqhfpss laflnltqnd factcehqsf lqwikdqrql 601 lvevermeca tpsdkqgmpv lslnitcqmn ktiigvsvls vlvvsvvavl vykfyfhlml 661 lagcikygrg eniydafviy ssqdedwvrn elvknleegv ppfqlclhyr dfipgvaiaa 721 niihegfhks rkvivvvsqh fiqsrwcife yeiaqtwqfl ssragiifiv lqkvektllr 781 qqvelyrlls rntyleweds vlgrhifwrr lrkalldgks wnpegtvgtg cnwqeatsi
```

In some embodiments, the biological material to be transplanted is one or more cells or cell types, one or more tissues or tissue types, or an organ or portion thereof. For example, the biological material to be transplanted is allogeneic biological material.

In some embodiments, the biological material to be transplanted is islet cells. In some embodiments, the islet cells are allogeneic islet cells.

In some embodiments, the biological material to be transplanted is or is derived from kidney, pancreas, liver, or intestine. For example, in some embodiments, the biological material to be transplanted is or is derived from one or more hepatocytes.

In some embodiments, the anti-TLR4 antibody that is used to contact the biological material prior to transplantation is the same anti-TLR4 antibody that is administered to the subject during and/or after the biological material has been transplanted.

In some embodiments, the anti-TLR4 antibody that is used to contact the biological material prior to transplantation is a different antibody than the anti-TLR4 antibody that is administered to the subject during and/or after the biological material has been transplanted.

In some embodiments, the antibody or immunologically active fragment thereof that specifically binds TLR4 is administered during and/or after transplantation in combination with one or more additional agents. In some embodiments, the anti-TLR4 antibody and the additional agent(s) are administered simultaneously. For example, the anti-TLR4 antibody and the additional agent(s) can be formulated in a single composition or administered as two or more separate compositions. In some embodiments, the anti-TLR4 antibody and the additional agent(s) are administered sequentially.

In some embodiments, the additional agent(s) is an immunosuppressive agent. For example, the additional agent(s) is selected from methotrexate, cyclosporin A, tacrolimus, sirolimus, everolimus, a corticosteroid, anti-thymocyte globulin, Infliximab, Etanercept and Adalimumab. The additional agent(s) can also include any compound or other molecule that exhibits an immunosuppressive effect.

In some embodiments, the antibody is an antibody or an immunologically active fragment thereof. In some embodiments, the antibody or immunologically active fragment thereof that binds TLR4 is a monoclonal antibody. In some embodiments, the antibody or immunologically active fragment thereof that binds TLR4 is a mouse, chimeric, humanized, fully human monoclonal antibody, domain antibody, single chain, $F_{ab}$, $F_{ab'}$ and $F_{(ab')2}$ fragments, scFvs, or an $F_{ab}$ expression library. In some embodiments, the anti-TLR4 antibodies also bind the human TLR4/MD-2 receptor complex.

In some embodiments, the antibody or immunologically active fragment thereof that binds TLR4 comprises a variable heavy chain complementarity determining region 1 ($V_H$ CDR1) comprising an amino acid sequence at least 90%, 92%, 95%, 96%, 97% 98%, 99% or more identical to the amino acid sequence of GGYSWH (SEQ ID NO: 1); a $V_H$ CDR2 region comprising an amino acid sequence at least 90%, 92%, 95%, 96%, 97% 98%, 99% or more identical to the amino acid sequence of YIHYSGYTDFNPSLKT (SEQ ID NO: 2); and a $V_H$ CDR3 region comprising an amino acid sequence at least 90%, 92%, 95%, 96%, 97% 98%, 99% or more identical to the amino acid sequence of KDPSDAFPY (SEQ ID NO: 3); a variable light chain complementarity determining region 1 ($V_L$ CDR1) region comprising an amino acid sequence at least 90%, 92%, 95%, 96%, 97% 98%, 99% or more identical to the amino acid sequence of RASQSISDHLH (SEQ ID NO: 4); a $V_L$ CDR2 region comprising an amino acid sequence at least 90%, 92%, 95%, 96%, 97% 98%, 99% or more identical to the amino acid sequence of YASHAIS (SEQ ID NO: 5); and a $V_L$ CDR3 region comprising an amino acid sequence at least 90%, 92%, 95%, 96%, 97% 98%, 99% or more identical to the amino acid sequence of QQGHSFPLT (SEQ ID NO: 6). In some embodiments, the antibody or immunologically active fragment thereof that binds TLR4 further comprises an amino acid sequence at least 90%, 92%, 95%, 96%, 97% 98%, 99% or more identical to the heavy chain variable amino acid sequence QVQLQESGPGLVKPSDTLSLTCAVSGYSITGGYSWH-WIRQPPGKGLEWMGYIHYSGYT DFNPSLKTRITIS-RDTSKNQFSLKLSSVTAVDTAVYYCARKDPSDAFPY-WGQGTLVTVSS (SEQ ID NO: 7) and an amino acid sequence at least 90%, 92%, 95%, 96%, 97% 98%, 99% or more identical to the light chain variable amino acid sequence EIVLTQSPDFQSVTPKEKVTITCRASQ-SISDHLHWYQQKPDQSPKLLIKYASHAISGVPSR FSGSGSGTDFTLTINSLEAEDAATYYC-QQGHSFPLTFGGGTKVEIK (SEQ ID NO: 8). In some embodiments, the antibody or immunologically active fragment thereof that binds TLR4 further comprises an amino acid sequence at least 90%, 92%, 95%, 96%, 97% 98%, 99% or more identical to the heavy chain amino acid sequence MGWSWIFLFLLSGTAGVHCQVQLQESG-PGLVKPSDTLSLTCAVSGYSITGGYSWHWIR QPPGK-GLEWMGYIHYSGYTDFNPSLKTRITIS-RDTSKNQFSLKLSSVTAVDTAVYYCAR KDPSDAFPYWGQGTLVTVSSASTKGPS-VFPLAPSSKSTSGGTAALGCLVKDYFPEPVTVS WNS-GALTSGVHTFPAVLQSSGLYSLSSV-VTVPSSSLGTQTYICNVNHKPSNTKVDKRVE PKSCDKTHTCPPCPAPELLGGPSVFLFP-PKPKDTLMISRTPEVTCVVVDVSHEDPEVKFN WYVDGVEVHNAKTKPREEQYNSTYRVVS-VLTVLHQDWLNGKEYKCKVSSKAFPAPIE KTISKAKGQPREPQVYTLPPSREEMTKN-QVSLTCLVKGFYPSDIAVEWESNGQPENNYK TTPPV-LDSDGSFFLYSKLTVDKSRWQQGNVF-SCSVMHEALHNHYTQKSLSLSPGK (SEQ ID NO: 9) and an amino acid sequence at least 90%, 92%, 95%, 96%, 97% 98%, 99% or more identical to the light chain amino acid sequence MEWSWVFLFFLSVTTGVHSEIVLTQSPD-FQSVTPKEKVTITCRASQSISDHLHWYQQKPD QSP-KLLIKYASHAISGVPSRFSGSGSGTD-FTLTINSLEAEDAATYYCQQGHSFPLTFGGGT KVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 10).

In some embodiments, anti-TLR4 antibody or immunologically active fragment thereof is or is derived from an antibody as described in PCT/IB2005/004206, filed Jun. 14, 2005 and published as WO 2007/110678, the contents of which are hereby incorporated by reference in their entirety.

In some embodiments, anti-TLR4 antibody or immunologically active fragment thereof is or is derived from an antibody as described in PCT application PCT/IB2008/003978, filed May 14, 2008 and published as WO 2009/101479, the contents of which are hereby incorporated by reference in their entirety.

In some embodiments, anti-TLR4 antibody or immunologically active fragment thereof is or is derived from the anti-TLR4 antibody known as HTA125, which is described, for example, in Shimazu, et al., J. Exp. Med., vol. 189:1777-1782 (1999); Nijhuis et al., Clin. Diag. Lab. Immunol., vol. 10(4): 558-63 (2003); and Pivarcsi et al., Intl. Immunopharm., vol. 15(6):721-730 (2003), the contents of each of which are hereby incorporated by reference in their entirety.

In some embodiments, the anti-TLR4 antibody or immunologically active fragment thereof is or is derived from a domain antibody such as, for example, the domain antibodies that bind TLR4 described in PCT application PCT/EP2009/055926, filed May 15, 2009 and published as WO 2009/13848, the contents of which are hereby incorporated by reference in their entirety.

In some embodiments, the anti-TLR4 antibody or immunologically active fragment thereof binds to an epitope comprising one or more amino acid residues on human TLR4 between residues 289 and 375 of SEQ ID NO: 11. For example, in some embodiments, the antibody or immunologically active fragment thereof binds to an epitope that comprises at least residues 328 and 329 of SEQ ID NO: 11. For example, in some embodiments, the antibody or immunologically active fragment thereof binds to an epitope that comprises at least residues 349 through 351 of SEQ ID NO: 11. For example, in some embodiments, the antibody or immunologically active fragment thereof binds to an epitope that comprises at least residues 369 through 371 of SEQ ID NO: 11. For example, in some embodiments, the antibody or immunologically active fragment thereof binds to an epitope that comprises at least residues 328, 329, 349 through 351 and 369 through 371 of SEQ ID NO: 11. For example, in some embodiments, the antibody or immunologically active fragment thereof binds to an epitope that comprises at least residues 293 through 295 of SEQ ID NO: 11. For example, in some embodiments, the antibody or immunologically active fragment thereof binds to an epitope that comprises at least residues 296 and 297 of SEQ ID NO: 11. For example, in some embodiments, the antibody or immunologically active fragment thereof binds to an epitope that comprises at least residues 319 through 321 of SEQ ID NO: 11. For example, in some embodiments, the antibody or immunologically active fragment thereof binds to an epitope that comprises at least residues 293 through 295, 296, 297 and 319 through 321 of SEQ ID NO: 11.

Pharmaceutical compositions according to the invention can include an antibody of the invention and a carrier. These pharmaceutical compositions can be included in kits, such as, for example, diagnostic kits.

DETAILED DESCRIPTION OF THE INVENTION

Figure 1:
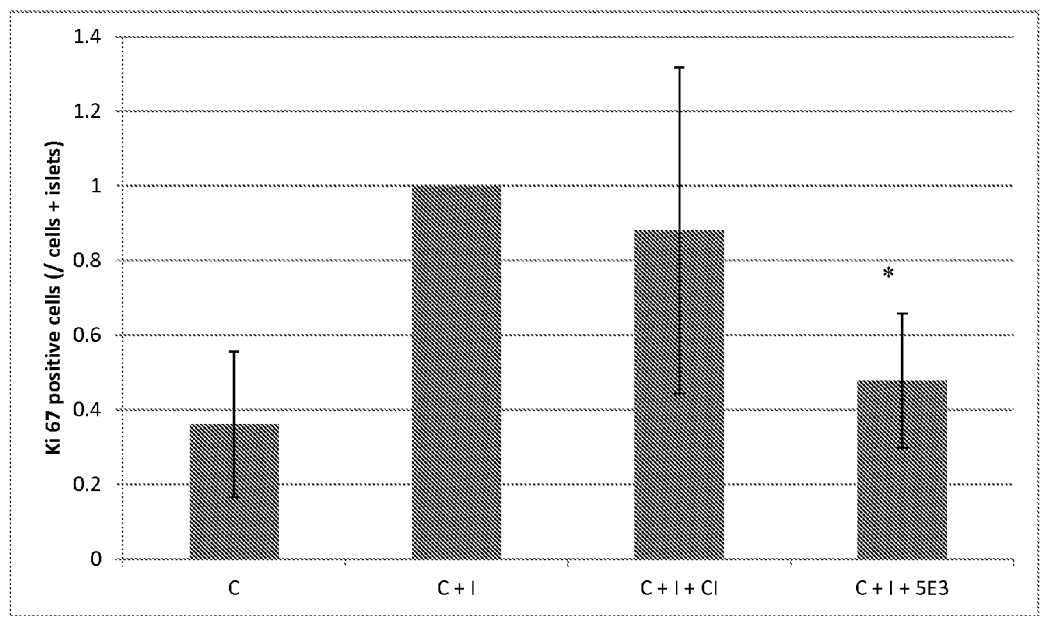
FIG. 1 is a graph that depicts proliferation of mouse lymph node cells in IMLR (Ki 67 positive cells). n=3; C=PBMC, I=islets, CI=control isotype.
Figure 2:
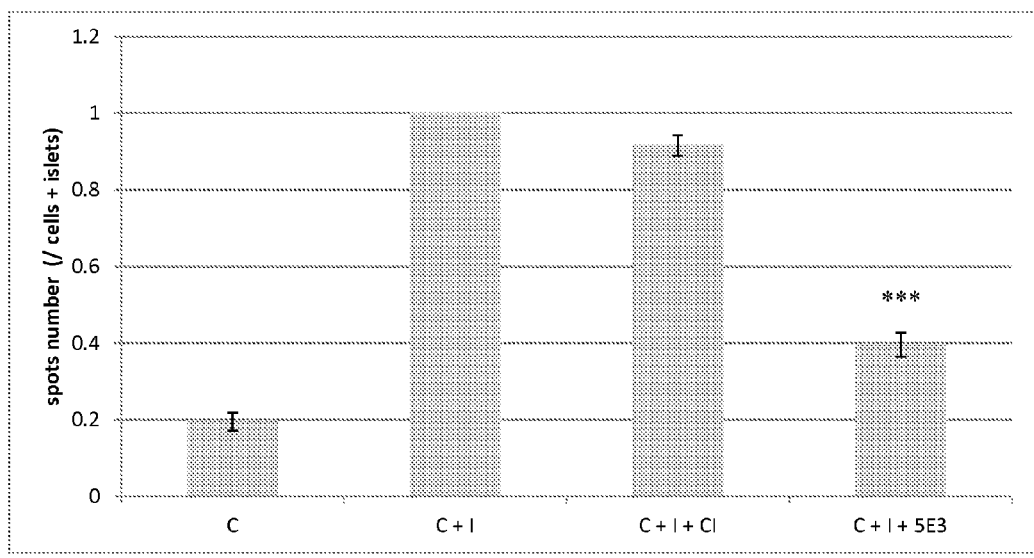
FIG. 2 is a graph that depicts mouse IFNγ secreting cells in IMLR (spots number). n=3; C=PBMC, I=islets, CI=control isotype.
Figure 3:
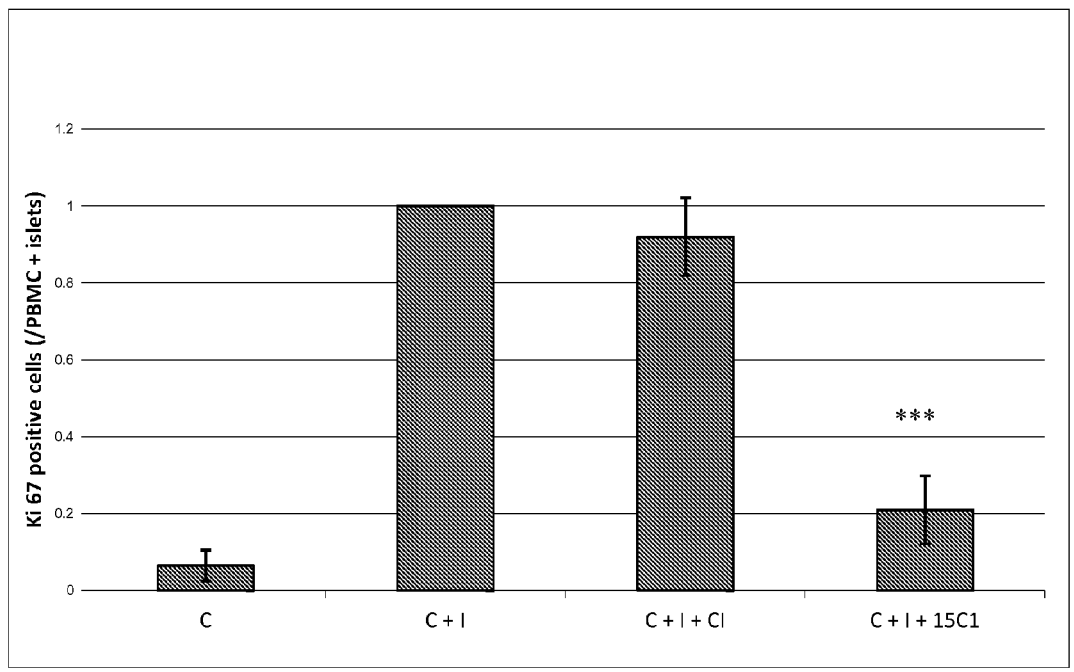
FIG. 3 is a graph that depicts proliferation of human PBMC in IMLR (Ki 67 positive cells). n=3; C=PBMC, I=islets, CI=control isotype.
Figure 4:
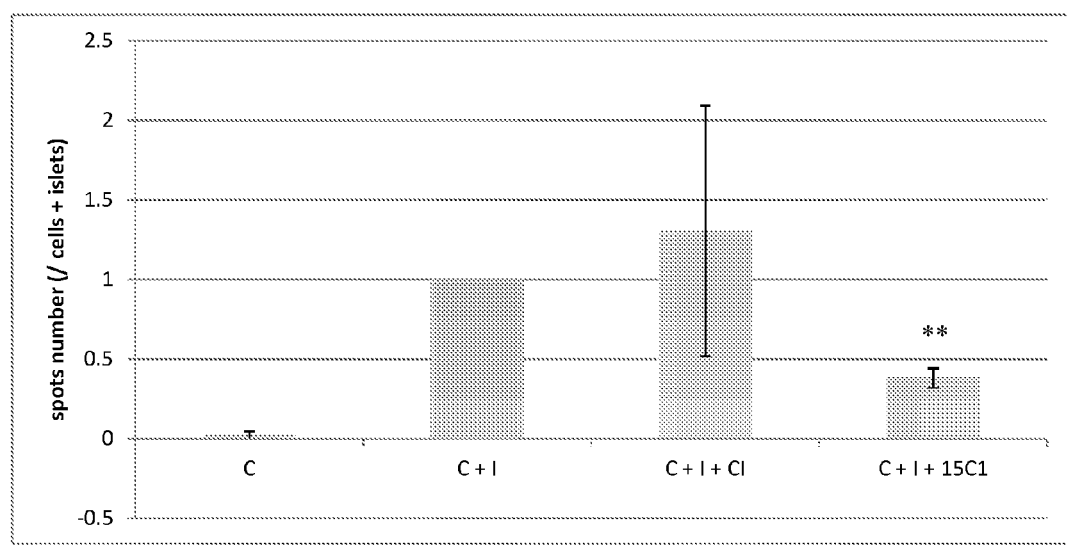
FIG. 4 is a graph that depicts human IFNγ secreting cells in IMLR (spots number). n=3; C=PBMC, I=islets, CI=control isotype.
Figure 5:
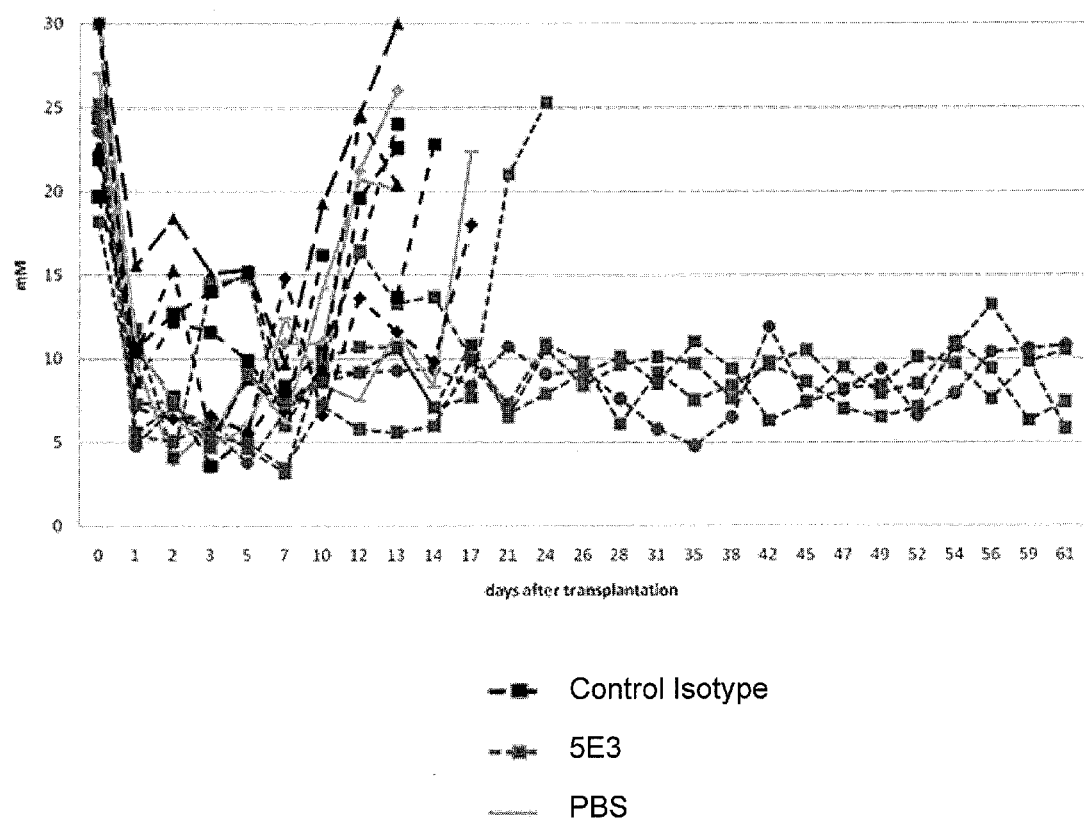
FIG. 5 is a graph that depicts blood glycaemia of transplanted mice (mM glc) where diabetic C57BL/6 mice were transplanted under the left kidney capsule with six hundred IEQ and injected intraperitoneally twice a week, from day 0 to day 28, with PBS (n=3), control isotype (n=6) or 5E3 (n=5).
Figure 6:
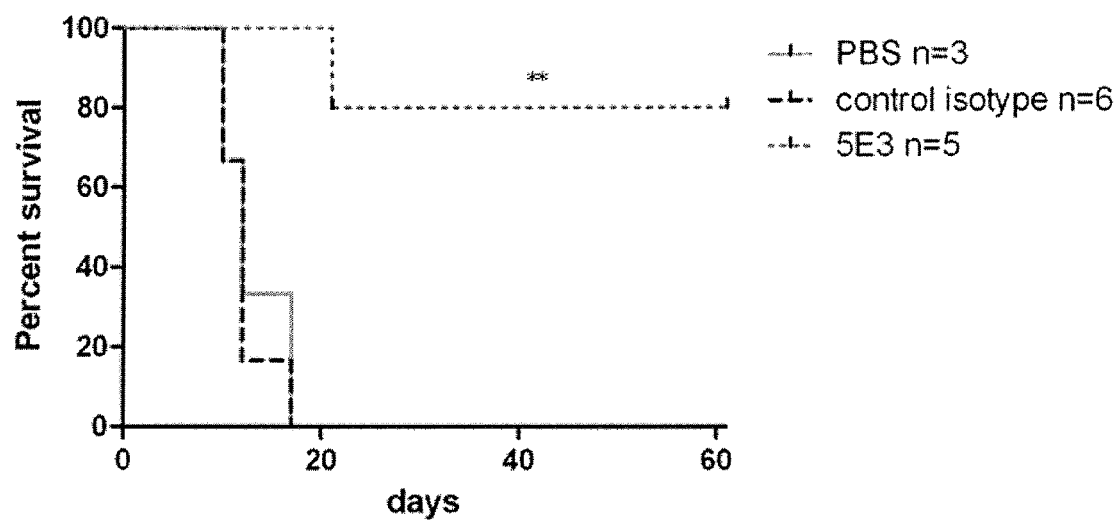
FIG. 6 is a graph that depicts graft survival in transplanted mice where diabetic C57BL/6 mice were transplanted under the left kidney capsule with six hundred IEQ and injected intraperitoneally twice a week, from day 0 to day 28, with PBS (n=3), control isotype (n=6) or 5E3 (n=5). Graft rejection was defined as three consecutive blood glycaemias>18 mM.

The present invention provides monoclonal antibodies (mAbs) that specifically bind Toll like Receptor 4, and more specifically, human TLR4. These anti-TLR4 antibodies are used in methods of inhibiting rejection of and/or prolonging survival of transplanted biological material in a subject using antibodies that specifically bind Toll-like receptor 4 (TLR4). Anti-TLR4 antibodies include antibodies that bind the human TLR4/MD-2 receptor complex and also bind TLR4 independently of the presence of MD-2.

Exemplary antibodies of the invention include, for example, the anti-TLR4 antibodies described in PCT/IB2005/004206, filed Jun. 14, 2005 and published as WO 2007/110678, the anti-TLR4 antibodies described in PCT application PCT/IB2008/003978, filed May 14, 2008 and published as WO 2009/101479, the contents of each of which are hereby incorporated by reference in their entirety, and commercially available antibodies such as HTA125.

Exemplary antibodies of the invention include, for example, the antibody referred to herein as NI-0101, which is also referred to herein and in the Figures as "hu15C1," which binds the human TLR4/MD2 complex and also binds TLR4 independently of the presence of MD-2. The sequences of the NI-0101 (hu15c1) antibody are shown below, with the CDR sequences underlined in the VH and VL amino acid sequences:

NI-0101 Heavy Chain Nucleotide Sequence:

NI-0101 heavy chain nucleotide sequence:

(SEQ ID NO: 12)
ATGGGATGGAGCTGGATCTTTCTCTTCCTCCTGTCAGGAACTGCAGGTGTACATTGCCAGGTGCAGCTTCAGGAGTC

CGGCCCAGGACTGGTGAAGCCTTCGGACACCCTGTCCCTCACCTGCGCTGTCTCTGGTTACTCCATCACCGGTGGTT

-continued

ATAGCTGGCACTGGATACGGCAGCCCCCAGGGAAGGGACTGGAGTGGATGGGGTATATCCACTACAGTGGTTACACT

GACTTCAACCCCTCCCTCAAGACTCGAATCACCATATCACGTGACACGTCCAAGAACCAGTTCTCCCTGAAGCTGAG

CTCTGTGACCGCTGTGGACACTGCAGTGTATTACTGTGCGAGAAAAGATCCGTCCGACGCCTTTCCTTACTGGGGCC

AAGGGACTCTGGTCACTGTCTCTTCCGCCTCCACCAAGGGCCCATCGGTCTTCCCCCTGGCACCCTCCTCCAAGAGC

ACCTCTGGGGGCACAGCGGCCCTGGGCTGCCTGGTCAAGGACTACTTCCCCGAACCGGTGACGGTGTCGTGGAACTC

AGGCGCCCTGACCAGCGGCGTGCACACCTTCCCGGCTGTCCTACAGTCCTCAGGACTCTACTCCCTCAGCAGCGTGG

TGACCGTGCCCTCCAGCAGCTTGGGCACCCAGACCTACATCTGCAACGTGAATCACAAGCCCAGCAACACCAAGGTG

GACAAGAGAGTTGAGCCCAAATCTTGTGACAAAACTCACACATGCCCACCGTGCCCAGCACCTGAACTCCTGGGGGG

ACCGTCAGTCTTCCTCTTCCCCCCAAAACCCAAGGACACCCTCATGATCTCCCGGACCCCTGAGGTCACATGCGTGG

TGGTGGACGTGAGCCACGAAGACCCTGAGGTCAAGTTCAACTGGTACGTGGACGGCGTGGAGGTGCATAATGCCAAG

ACAAAGCCGCGGGAGGAGCAGTACAACAGCACGTACCGTGTGGTCAGCGTCCTCACCGTCCTGCACCAGGACTGGCT

GAATGGCAAGGAGTACAAATGCAAGGTCTCCAGTAAAGCTTTCCCTGCCCCCATCGAGAAAACCATCTCCAAAGCCA

AAGGGCAGCCCCGAGAACCACAGGTGTACACCCTGCCCCCATCCCGGGAGGAGATGACCAAGAACCAGGTCAGCCTG

ACCTGCCTGGTCAAAGGCTTCTATCCCAGCGACATCGCCGTGGAGTGGGAGAGCAATGGGCAGCCGGAGAACAACTA

CAAGACCACGCCTCCCGTGCTGGACTCCGACGGCTCCTTCTTCCTCTATAGCAAGCTCACCGTGGACAAGAGCAGGT

GGCAGCAGGGGAACGTCTTCTCATGCTCCGTGATGCATGAGGCTCTGCACAACCACTACACGCAGAAGAGCCTCTCC

CTGTCTCCGGGTAAATAG

NI-0101 heavy chain amino acid sequence:
(SEQ ID NO: 9)
MGWSWIFLFLLSGTAGVHCQVQLQESGPGLVKPSDTLSLTCAVSGYSITGGYSWHWIRQPPGKGLEWMGYIHYSGYT

DFNPSLKTRITISRDTSKNQFSLKLSSVTAVDTAVYYCARKDPSDAFPYWGQGTLVTVSSASTKGPSVFPLAPSSKS

TSGGTAALGCLVKDYFPEPVTVSWNSGALTSGVHTFPAVLQSSGLYSLSSVVTVPSSSLGTQTYICNVNHKPSNTKV

DKRVEPKSCDKTHTCPPCPAPELLGGPSVFLFPPKPKDTLMISRTPEVTCVVVDVSHEDPEVKFNWYVDGVEVHNAK

TKPREEQYNSTYRVVSVLTVLHQDWLNGKEYKCKVSSKAFPAPIEKTISKAKGQPREPQVYTLPPSREEMTKNQVSL

TCLVKGFYPSDIAVEWESNGQPENNYKTTPPVLDSDGSFFLYSKLTVDKSRWQQGNVFSCSVMHEALHNHYTQKSLS

LSPGK

NI-0101 light chain nucleotide sequence:
(SEQ ID NO: 13)
ATGGAATGGAGCTGGGTCTTTCTCTTCTTCCTGTCAGTAACTACAGGTGTCCACTCCGAAATTGTGTTGACGCAGTC

TCCAGACTTTCAGTCTGTGACTCCAAAGGAAAAAGTCACCATCACCTGCAGGGCCAGTCAGAGTATCAGCGACCACT

TACACTGGTACCAACAGAAACCTGATCAGTCTCCCAAGCTCCTCATCAAATATGCTTCCCATGCCATTTCTGGGGTC

CCATCGAGGTTCAGTGGCAGTGGGTCTGGGACAGACTTCACTCTCACCATCAATAGCCTAGAGGCTGAAGATGCTGC

AACGTATTACTGTCAGCAGGGTCACAGTTTTCCGCTCACTTTCGGCGGAGGGACCAAGGTGGAGATCAAACGTACGG

TGGCTGCACCATCTGTCTTCATCTTCCCGCCATCTGATGAGCAGTTGAAATCTGGAACTGCCTCTGTTGTGTGCCTG

CTGAATAACTTCTATCCCAGAGAGGCCAAAGTACAGTGGAAGGTGGATAACGCCCTCCAATCGGGTAACTCCCAGGA

GAGTGTCACAGAGCAGGACAGCAAGGACAGCACCTACAGCCTCAGCAGCACCCTGACGCTGAGCAAAGCAGACTACG

AGAAACACAAAGTCTACGCCTGCGAAGTCACCCATCAGGGCCTGAGCTCGCCCGTCACAAAGAGCTTCAACAGGGGA

GAGTGTTAG

NI-0101 light chain amino acid sequence:
(SEQ ID NO: 10)
MEWSWVFLFFLSVTTGVHSEIVLTQSPDFQSVTPKEKVTITCRASQSISDHLHWYQQKPDQSPKLLIKYASHAISGV PSRFSGSGSGTDFTLTINSLEAEDAATYYCQQGHSFPLTFGGGTKVEIKRTVAAPSVFIFPPSDEQLKSGTASVVCL

```
LNNFYPREAKVQWKVDNALQSGNSQESVTEQDSKDSTYSLSSTLTLSKADYEKHKVYACEVTHQGLSSPVTKSFNRG
EC
```

The NI-0101 (hu15c1) antibody includes VH CDRs having the sequences GGYSWH (SEQ ID NO: 1), YIHYSGYTD-FNPSLKT (SEQ ID NO: 2), and KDPSDAFPY (SEQ ID NO: 3), and VL CDRs having the sequences RASQSISDHLH (SEQ ID NO: 4), YASHAIS (SEQ ID NO: 5) and QQGHS-FPLT (SEQ ID NO: 6).

The amino acid and nucleic acid sequences of the heavy chain variable (VH) and light chain variable (VL) regions of the anti-TLR4/MD2 antibodies are shown below. The amino acids encompassing the complementarity determining regions (CDR) as defined by Chothia et al. 1989, E. A. Kabat et al., 1991 are highlighted in underlined and italicized text below. (See Chothia, C, et al., Nature 342:877-883 (1989); Kabat, E A, et al., Sequences of Protein of immunological interest, Fifth Edition, US Department of Health and Human Services, US Government Printing Office (1991)).

Anti-TLR4 antibodies include the antibodies described in co-pending U.S. application Ser. Nos. 11/009,939, filed Dec. 10, 2004 and 11/151,916, filed Jun. 15, 2004 and in WO 05/065015, filed Dec. 10, 2004 and PCT/US2005/020930, filed Jun. 15, 2004, each of which is hereby incorporated by reference in its entirety. Several exemplary antibodies include the antibodies referred to therein as 18H10, 16G7, 15C1 and 7E3.

Anti-TLR4 antibodies include the antibodies described in co-pending U.S. application Ser. No. 11/151,916, filed Jun. 15, 2004 (U.S. Patent Publication No. US 2008-0050366 A1) and in PCT/IB2005/004206, filed Jun. 15, 2004 (PCT Publication No. WO 07/110,678), each of which is hereby incorporated by reference in its entirety. The sequences of several exemplary antibodies are shown below.

```
15C1 Hu V_H version 4-28
                                                            (SEQ ID NO: 14)
QVQLQESGPG LVKPSDTLSL TCAVSGYSI X_1 GGYSWHWIRQ PPGKGLEW X_2G

YIHYSGYTDF NPSLKTR X_3T X_4 SRDTSKNQFS LKLSSVTAVD TAVYYCARKD

PSDGFPYWGQ GTLVTVSS

CDR 1: GGYSWH (SEQ ID NO: 1)
CDR 2: YIHYSGYTDFNPSLKT (SEQ ID NO: 2)
CDR 3: KDPSDGFPY (SEQ ID NO: 3)
Where X_1 is Thr or Ser
Where X_2 is Ile or Met
Where X_3 is Val or Ile
Where X_4 is Met or Ile 15C1 Hu V_H version 3-66
                                                            (SEQ ID NO: 15)
EVQLVESGGG LVQPGGSLRL SCAX_1SGYSIT GGYSWHWVRQ APGKGLEWX_2S

YIHYSGYTDF NPSLKTRFTI SRDNSKNTX_3Y LQMNSLRAED TAVYYCARKD

PSDGFPYWGQ GTLVTVSS

CDR 1: GGYSWH (SEQ ID NO: 1)
CDR 2: YIHYSGYTDFNPSLKT (SEQ ID NO: 2)
CDR 3: KDPSDGFPY (SEQ ID NO: 3)
Where X_1 is Ala or Val
Where X_2 is Val or Met
Where X_3 is Leu or Phe 15C1 Hu VL version L6
                                                            (SEQ ID NO: 16)
EIVLTQSPAT LSLSPGERAT LSCRASQSIS DHLHWYQQKP GQAPRLLIX_1Y

ASHAISGIPA RFSGSGSGTD FTLTISSLEP EDFAVYYCQN GHSFPLTFGG GTKVEIK

CDR1: RASQSISDHLH (SEQ ID NO: 4)
CDR2: YASHAIS (SEQ ID NO: 5)
CDR3: QNGHSFPLT (SEQ ID NO: 17)
Where X_1 is Lys or Tyr 15C1 Hu VL version A26
                                                            (SEQ ID NO: 18)
EIVLTQSPDF QSVTPKEKVT ITCRASQSIS DHLHWYQQKP DQSPKLLIKY

ASHAISGVPS RFSGSGSGTD FTLTINSLEA EDAATYYCQN GHSFPLTFGG GTKVEIK

CDR1: RASQSISDHLH (SEQ ID NO: 4)
CDR2: YASHAIS (SEQ ID NO: 5)
```

CDR3: QNGHSFPLT (SEQ ID NO: 17)

18H10 Hu VH version 1-69
(SEQ ID NO: 19)
QVQLVQSGAE VKKPGSSVKV SCKASGFNIK DSYIHWVRQA PGQGLEWX₁GW

TDPENVNSIY DPRFQGRVTI TADX₂STSTAY X₃ELSSLRSED TAVYYCARGY

NGVYYAMDYW GQGTTVTVSS

CDR1: DSYIH (SEQ ID NO: 20)
CDR2: WTDPENVNSIYDPRFQG (SEQ ID NO: 21)
CDR3: GYNGVYYAMDY (SEQ ID NO: 22)
Where X₁ is Met or Ile
Where X₂ is Lys or Thr
Where X₃ is Met or Leu 18H10 Hu VL version L6
(SEQ ID NO: 23)
EIVLTQSPAT LSLSPGERAT LSCSASSSVI YMHWYQQKPG QAPRLLIYRT

YNLASGIPAR FSGSGSGTDX₁ TLTISSLEPE DFAVYYCHQW SSFPYTFGQG TKVEIK

CDR1: SASSSVIYMH (SEQ ID NO: 24)
CDR2: RTYNLAS (SEQ ID NO: 25)
CDR3: HQWSSFPYT (SEQ ID NO: 26)
Where X₁ is Phe or Tyr 7E3 Hu VH version 2-70
(SEQ ID NO: 27)
QVTLRESGPA LVKPTQTLTL TCTFSGFSLX₁ TYNIGVGWIR QPPGKALEWL

AHIWWNDNIY YNTVLKSRLT X₂SKDTSKNQV VLTMTNMDPV DTATYYCX₃R M

AEGRYDAMDY WGQGTLVTVS S

CDR1: TYNIGVG (SEQ ID NO: 28)
CDR2: HIWWNDNIYYNTVLKS (SEQ ID NO: 29)
CDR3: MAEGRYDAMDY (SEQ ID NO: 30)
Where X₁ is Ser or Thr
Where X₂ is Ile or Phe
Where X₃ is Ile or Ala 7E3 Hu VH version 3-66
(SEQ ID NO: 31)
EVQLVESGGG LVQPGGSLRL SCAX₁SGFSLT TYNIGVGWVR QAPGKGLEWX₂

SHIWWNDNIY YNTVLKSRLT X₃SX₄DNSKNTX₅ YLQMNSLRAE DTAVYYCX₆R M

AEGRYDAMDY WGQGTLVTVS S

CDR1: TYNIGVG (SEQ ID NO: 28)
CDR2: HIWWNDNIYYNTVLKS (SEQ ID NO: 29)
CDR3: MAEGRYDAMDY (SEQ ID NO: 30)
Where X₁ is Phe or Ala
Where X₂ is Val or Leu
Where X₃ is Ile or Phe
Where X₄ is Lys or Arg
Where X₅ is Leu or Val
Where X₆ is Ile or Ala 7E3 Hu VL version L19
(SEQ ID NO: 32)
DIQMTQSPSS VSASVGDRVT ITCRASQDIT NYLNWYQQKP GKAPKLLIYY

TSKLHSGVPS RFSGSGSTD X₁TLTISSLQP EDFATYX₂CQQ GNTFPWTFGG GTKVEIK

CDR1: RASQDITNYLN (SEQ ID NO: 33)
CDR2: YTSKLHS (SEQ ID NO: 34)
CDR3: QQGNTFPWT (SEQ ID NO: 35)
Where X₁ is Phe or Tyr
Where X₂ is Tyr or Phe Anti-TLR4 antibodies include the antibodies described in PCT/IB2008/003978, filed May 14, 2008 (PCT Publication No. WO 2009/101479), the contents of which are hereby incorporated by reference in their entirety. These anti-TLR4 antibodies are modified to include one or more mutations in the CDR3 portion. The sequences of several exemplary antibodies are shown below.

```
15C1 humanized VH mutant 1 amino acid sequence:
                                                 (SEQ ID NO: 36)
QVQLQESGPGLVKPSDTLSLTCAVSGYSITGGYSWHWIRQPPGKGLEWMGYIHYSGYTDFNPSL

KTRITISRDTSKNQFSLKLSSVTAVDTAVYYCARKDPSDAFPYWGQGTLVTVSS

15C1 humanized VH mutant 1 nucleic acid sequence:
                                                 (SEQ ID NO: 37)
CAGGTGCAGCTTCAGGAGTCCGGCCCAGGACTGGTGAAGCCTTCGGACACCCTGTCCCTCACCT

GCGCTGTCTCTGGTTACTCCATCACCGGTGGTTATAGCTGGCACTGGATACGGCAGCCCCCAGG

GAAGGGACTGGAGTGGATGGGGTATATCCACTACAGTGGTTACACTGACTTCAACCCCTCCCTC

AAGACTCGAATCACCATATCACGTGACACGTCCAAGAACCAGTTCTCCCTGAAGCTGAGCTCTG

TGACCGCTGTGGACACTGCAGTGTATTACTGTGCGAGAAAAGATCCGTCCGACGCCTTTCCTTA

CTGGGGCCAAGGGACTCTGGTCACTGTCTCTTCC

15C1 humanized VH mutant 2 amino acid sequence:
                                                 (SEQ ID NO: 38)
QVQLQESGPGLVKPSDTLSLTCAVSGYSITGGYSWHWIRQPPGKGLEWMGYIHYSGYTDFNPSL

KTRITISRDTSKNQFSLKLSSVTAVDTAVYYCARKDPSEGFPYWGQGTLVTVSS

15C1 humanized VH mutant 2 nucleic acid sequence:
                                                 (SEQ ID NO: 39)
CAGGTGCAGCTTCAGGAGTCCGGCCCAGGACTGGTGAAGCCTTCGGACACCCTGTCCCTCACCT

GCGCTGTCTCTGGTTACTCCATCACCGGTGGTTATAGCTGGCACTGGATACGGCAGCCCCCAGG

GAAGGGACTGGAGTGGATGGGGTATATCCACTACAGTGGTTACACTGACTTCAACCCCTCCCTC

AAGACTCGAATCACCATATCACGTGACACGTCCAAGAACCAGTTCTCCCTGAAGCTGAGCTCTG

TGACCGCTGTGGACACTGCAGTGTATTACTGTGCGAGAAAAGATCCGTCCGAGGGATTTCCTTA

CTGGGGCCAAGGGACTCTGGTCACTGTCTCTTCC

15C1 humanized VL mutant 1 amino acid sequence:
                                                 (SEQ ID NO: 40)
EIVLTQSPDFQSVTPKEKVTITCRASQSISDHLHWYQQKPDQSPKLLIKYASHAISGVPSRFSG

SGSGTDFTLTINSLEAEDAATYYCQNSHSFPLTFGGGTKVEIK

15C1 humanized VL mutant 1 nucleic acid sequence:
                                                 (SEQ ID NO: 41)
GAAATTGTGTTGACGCAGTCTCCAGACTTTCAGTCTGTGACTCCAAAGGAAAAAGTCACCATCA

CCTGCAGGGCCAGTCAGAGTATCAGCGACCACTTACACTGGTACCAACAGAAACCTGATCAGTC

TCCCAAGCTCCTCATCAAATATGCTTCCCATGCCATTTCTGGGGTCCCATCGAGGTTCAGTGGC

AGTGGGTCTGGGACAGACTTCACTCTCACCATCAATAGCCTAGAGGCTGAAGATGCTGCAACGT

ATTACTGTCAGAATAGTCACAGTTTTCCGCTCACTTTCGGCGGAGGGACCAAGGTGGAGATCAA

A

15C1 humanized VL mutant 2 amino acid sequence:
                                                 (SEQ ID NO: 42)
EIVLTQSPDFQSVTPKEKVTITCRASQSISDHLHWYQQKPDQSPKLLIKYASHAISGVPSRFSG

SGSGTDFTLTINSLEAEDAATYYCQQGHSFPLTFGGGTKVEIK

15C1 humanized VL mutant 2 nucleic acid sequence:
                                                 (SEQ ID NO: 43)
GAAATTGTGTTGACGCAGTCTCCAGACTTTCAGTCTGTGACTCCAAAGGAAAAAGTCACCATCA

CCTGCAGGGCCAGTCAGAGTATCAGCGACCACTTACACTGGTACCAACAGAAACCTGATCAGTC
```

-continued

TCCCAAGCTCCTCATCAAATATGCTTCCCATGCCATTTCTGGGGTCCCATCGAGGTTCAGTGGC

AGTGGGTCTGGGACAGACTTCACTCTCACCATCAATAGCCTAGAGGCTGAAGATGCTGCAACGT

ATTACTGTCAGCAGGGTCACAGTTTTCCGCTCACTTTCGGCGGAGGGACCAAGGTGGAGATCAA

A

15C1 humanized VL mutant 3 amino acid sequence:
(SEQ ID NO: 44)
EIVLTQSPDFQSVTPKEKVTITCRASQSISDHLHWYQQKPDQSPKLLIKYASHAISGVPSRFSG

SGSGTDFTLTINSLEAEDAATYYCQNSSSFPLTFGGGTKVEIK

15C1 humanized VL mutant 3 nucleic acid sequence:
(SEQ ID NO: 45)
GAAATTGTGTTGACGCAGTCTCCAGACTTTCAGTCTGTGACTCCAAAGGAAAAAGTCACCATCA

CCTGCAGGGCCAGTCAGAGTATCAGCGACCACTTACACTGGTACCAACAGAAACCTGATCAGTC

TCCCAAGCTCCTCATCAAATATGCTTCCCATGCCATTTCTGGGGTCCCATCGAGGTTCAGTGGC

AGTGGGTCTGGGACAGACTTCACTCTCACCATCAATAGCCTAGAGGCTGAAGATGCTGCAACGT

ATTACTGTCAGAATAGTAGTAGTTTTCCGCTCACTTTCGGCGGAGGGACCAAGGTGGAGATCAA

A

15C1 humanized VL mutant 4 amino acid sequence:
(SEQ ID NO: 46)
EIVLTQSPDFQSVTPKEKVTITCRASQSISDHLHWYQQKPDQSPKLLIKYASHAISGVPSRFSG

SGSGTDFTLTINSLEAEDAATYYCQQSHSFPLTFGGGTKVEIK

15C1 humanized VL mutant 4 nucleic acid sequence:
(SEQ ID NO: 47)
GAAATTGTGTTGACGCAGTCTCCAGACTTTCAGTCTGTGACTCCAAAGGAAAAAGTCACCATCA

CCTGCAGGGCCAGTCAGAGTATCAGCGACCACTTACACTGGTACCAACAGAAACCTGATCAGTC

TCCCAAGCTCCTCATCAAATATGCTTCCCATGCCATTTCTGGGGTCCCATCGAGGTTCAGTGGC

AGTGGGTCTGGGACAGACTTCACTCTCACCATCAATAGCCTAGAGGCTGAAGATGCTGCAACGT

ATTACTGTCAGCAGAGTCACAGTTTTCCGCTCACTTTCGGCGGAGGGACCAAGGTGGAGATCAA

A

DEFINITIONS

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, domain antibody, single chain, $F_{ab}$, $F_{ab'}$ and $F_{(ab')2}$ fragments, scFvs, and an $F_{ab}$ expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is said to specifically bind an antigen when the dissociation constant is $\leq 1$ µM; preferably $\leq 100$ nM and most preferably $\leq 10$ nM.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to the Toll-like Receptor 4 (TLR4)/MD-2 complex or to TLR4 when not complexed to MD-2, when the equilibrium binding constant ($K_d$) is $\leq 1$ µM, preferably $\leq 100$ nM, more preferably $\leq 10$ nM, and most preferably $\leq 100$ pM to about 1 pM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Polynucleotides in accordance with the invention include the nucleic acid molecules encoding the heavy chain immunoglobulin molecules shown herein, and nucleic acid molecules encoding the light chain immunoglobulin molecules shown herein.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of marine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the invention comprise the heavy chain immunoglobulin molecules shown herein, and the light chain immunoglobulin molecules shown herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means a polymeric boron of nucleotides of at least 10 bases in length, either ribonucleotides or deoxynucleotides or a modified form of either type of nucleotide. The term includes single and double stranded forms of DNA.

The term oligonucleotide referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the invention are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes Oligonucleotides linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman Adv. Appl. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2nd Edition, E. S. Golub and D. R. Gren, Eds., Sinauer Associates, Sunderland7 Mass. (1991)). Stereoisomers (e.g., D-amino acids) of the twenty conventional amino acids, unnatural amino acids such as $\alpha$-, $\alpha$-disubstituted amino acids, N-alkyl amino acids, lactic acid, and other unconventional amino acids may also be suitable components for polypeptides of the present invention. Examples of unconventional amino acids include: 4 hydroxyproline, $\gamma$-carboxyglutamate, $\epsilon$-N,N,N-trimethyllysine, $\epsilon$-N-acetyllysine, O-phosphoserine, N-acetylserine, N-formylmethionine, 3-methylhistidine, 5-hydroxylysine, $\sigma$-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and which are 5' to the 5' end of the RNA transcript are referred to as "upstream sequences", sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxy-terminal deletion, but where the remaining amino acid sequence is identical to the corresponding positions in the naturally-occurring sequence deduced, for example, from a full length cDNA sequence. Fragments typically are at least 5, 6, 8 or 10 amino acids long, preferably at least 14 amino acids long more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has specific binding to TLR4/MD2 complex or TLR4 alone, under suitable binding conditions. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, J. Adv. Drug Res. 15:29 (1986), Veber and Freidinger TINS p. 392 (1985); and Evans et al. J. Med. Chem. 30:1229 (1987). Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —$CH_2NH$—, —$CH_2S$—, —$CH_2$—$CH_2$—, —CH=CH— (cis and trans), —$COCH_2$—, $CH(OH)CH_2$—, and —$CH_2SO$—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992)); for example, by adding internal cysteine residues capable of forming intramolecular disulfide bridges which cyclize the peptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^3H$, $^{14}C$, $^{15}N$, $^{35}S$, $^{90}Y$, $^{99}Tc$, $^{111}In$, $^{125}I$, $^{131}I$) fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

The term "antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present.

Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term patient includes human and veterinary subjects.

Antibodies

Monoclonal antibodies of the invention (e.g., murine monoclonal, humanized antibodies or fully human monoclonal antibodies) specifically bind TLR4. Also included in the invention are antibodies that bind to the same epitope as the antibodies described herein. For example, antibodies of the invention that specifically bind TLR4 and/or the TLR4/MD-2 complex bind to an epitope that includes one or more amino acid residues on human TLR4 shown below:

(SEQ ID NO: 11)

```
  1 mmsasrlagt lipamaflsc vrpeswepcv evvpnityqc melnfykipd nlpfstknld
 61 lsfnplrhlg sysffsfpel qvldlsrcei qtiedgayqs lshlstlilt gnpiqslalg
121 afsglsslqk lvavetnlas lenfpighlk tlkelnvahn liqsfklpey fsnltnlehl
181 dlssnkiqsi yctdlrvlhq mpllnlsldl slnpmnfiqp gafkeirlhk ltlrnnfdsl
241 nvmktciqgl aglevhrlvl gefrnegnle kfdksalegl cnltieefrl ayldyylddi
301 idlfncltnv ssfslvsvti ervkdfsynf gwqhlelvnc kfgqfptlkl kslkrltfts
361 nkggnafsev dlpslefldl srnglsfkgc csqsdfgtts lkyldlsfng vitmssnflg
421 leglehldfq hsnlkqmsef svflslrnli yldishthtr vafngifngl sslevlkmag
481 nsfqenflpd iftelrnltf ldlsqcqleq lsptafnsls slqvlnmshn nffsldtfpy
541 kclnslqvld yslnhimtsk kqelqhfpss laflnltqnd factcehqsf lqwikdqrql
601 lvevermeca tpsdkqgmpv lslnitcqmn ktiigvsvls vlvvsvvavl vykfyfhlml
661 lagcikygrg eniydafviy ssqdedwvrn elvknleegv ppfqlclhyr dfipgvaiaa
```

```
721 niihegfhks rkvivvvsqh fiqsrwcife yeiaqtwqfl ssragiifiv lqkvektllr 781 qqvelyrlls rntyleweds vlgrhifwrr lrkalldgks wnpegtvgtg cnwqeatsi
```

Those skilled in the art will recognize that it is possible to determine, without undue experimentation, if a monoclonal antibody (e.g., a murine monoclonal or humanized antibody) has the same specificity as a monoclonal antibody used in the methods described herein by ascertaining whether the former prevents the latter from binding to the TLR4/MD-2 complex or to TLR4 when not complexed to MD-2. If the monoclonal antibody being tested competes with the monoclonal antibody of the invention, as shown by a decrease in binding by the monoclonal antibody of the invention, then the two monoclonal antibodies bind to the same, or a closely related, epitope. An alternative method for determining whether a monoclonal antibody has the specificity of monoclonal antibody of the invention is to pre-incubate the monoclonal antibody of the invention with the TLR4/MD-2 complex or a soluble TLR4 protein (with which it is normally reactive), and then add the monoclonal antibody being tested to determine if the monoclonal antibody being tested is inhibited in its ability to bind the TLR4/MD-2 complex or to bind TLR4 and TLR4 complexed with MD-2. If the monoclonal antibody being tested is inhibited then, in all likelihood, it has the same, or functionally equivalent, epitopic specificity as the monoclonal antibody of the invention.

Use of Anti-TLR4 Antibodies

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2): 210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the invention, which include an anti-TLR4 antibody, are used to prevent transplant rejection and/or prolong survival of a transplant.

Efficaciousness of treatment is determined in association with any known method for diagnosing or treating transplant rejection or other transplant related disorders. Prolonging the survival of transplanted biological material or otherwise preventing transplant rejection in a subject indicates that the antibody confers a clinical benefit.

Anti-TLR4 antibodies be administered in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

In some embodiments, the antibody contains a detectable label. Antibodies are polyclonal, or more preferably, monoclonal. An intact antibody, or a fragment thereof (e.g., $F_{ab}$, scFv, or $F_{(ab)2}$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Pharmaceutical Compositions

The antibodies or soluble chimeric polypeptides of the invention (also referred to herein as "active compounds"), and derivatives, fragments, analogs and homologs thereof, can be incorporated into pharmaceutical compositions suitable for administration. Such compositions typically comprise the antibody or soluble chimeric polypeptide and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The invention will be further described in the following examples, which do not limit the scope of the invention described in the claims.

EXAMPLES

The Examples and data provided herein assess the role of TLR4 in mediating an immune response to allogeneic islets. Briefly, purified human or murine (DBA1) islets were co-cultured respectively with allogeneic PBMC or lymph node cells, in the presence or absence of anti-human or anti-mouse TLR4 mAb, or relevant isotype controls. Proliferating cells were assessed using Ki67 staining, and IFNγ-secreting cells were assessed using ELISPOT assay. DBA1 islets, cultured 24 h in vitro with the anti-mouse mAbs, were transplanted under the kidney capsule of C57BL/6 diabetic mice, injected twice a week intraperitoneally with the anti-mouse mAbs from day 0 to 28 after transplantation. Blood sugar was monitored twice a week. In vitro results showed a decrease in proliferation of 79±2% (p<0.001) and 67±16% (p=0.05) in the human and murine mixed islet-lymphocyte cultures, respectively, as compared to controls. Similarly, a decrease of 62±9% (N=3, p<0.05) and 64±10% (N=3, p<0.05) in the numbers of IFNγ-secreting cells was observed. In vivo, treatment with the anti-mouse TLR4 mAb prolonged islet graft survival to >60 days in 80% of animals (N=5), contrasting with a graft survival of 0% at 17 days in the isotype control-(N=6) and buffer-treated mice (N=3). These results demonstrate that TLR4 blockade can efficiently modulate the immunogenicity of human or murine islets in vitro and is able to achieve indefinite islet graft survival in vivo.

While the studies described herein use allogeneic islets, the materials, methods, and examples are illustrative only and are not intended to be limiting.

Example 1

Materials and methods for the generation of 15C1 and 5E3 monoclonal antibodies: The hu15C1 antibody, also referred to herein as NI-0101, was generated and tested as described in PCT application PCT/IB2008/003978, filed May 14, 2008 and published as WO 2009/101479, the contents of which are hereby incorporated by reference in their entirety. The 5E3 monoclonal antibody is a monoclonal antibody that binds mouse TLR4. (See Daubeuf et al., "TLR4/MD-2 Monoclonal Antibody Therapy Affords Protection in Experimental Models of Septic Shock," J Immunol vol. 179:6107-6114 (1997).

Control antibodies: Human control isotype was purchased from SIGMA® (ref number I5029) and FITC anti-Ki-67 Set from BD Pharmingen™ (Franklin Lakes N.J.).

Human islets: Pancreases were obtained from brain-dead multi-organ donors through Swisstransplant and the French Agence de la Biomédecine.

Islets were isolated using the automated method described by Ricordi with local modifications. (See e.g., Ricordi et al., "Automated method for isolation of human pancreatic islets," Diabetes, vol. 37(4): 413-20 (1988); Ricordi et al., "Automated islet isolation from human pancreas," Diabetes, vol. 38 Suppl 1:140-2 (1989)). Collagenase NB1 (Serva Electrophoresis, Heidelberg, Germany) was used. Islets were purified on a continuous Biocoll gradient (Biochrom, Berlin, Germany) with a refrigerated COBE cell processor (COBE 2991; Cobe, Lakewood, Colo.).

Islets were incubated overnight in non-adherent 60-mm diameter Petri dishes containing 5 ml of CMRL-10% FCS (10% foetal calf serum, 11.2 mM glucose, 110 µg/ml sodium pyruvate and supplemented with 110 units/ml penicillin, 110 µg/ml streptomycin, and 50 µg/ml gentamycin) with or without 1.5 nM 15C1 antibody or control isotype.

Animals: Two-month-old male C57BL/6 and DBA1 mice were purchased from Janvier (Le Genest-St-Isle, France). All animals were kept in the animal facilities at the University of Geneva with free access to food and water. All experiments were conducted under protocols reviewed and approved by institutional animal care and use committee.

Mouse islets: Islets of Langerhans were isolated by collagenase digestion of pancreases from male DBA1 mice, followed by Ficoll purification using a modification of the method of Sutton et al. (Sutton et al., "Human pancreatic islet isolation with increased incubation temperatures and variable density gradients," Transplant Proc., vol. 22: 758-59 (1990).

Islets were incubated overnight in non-adherent 60-mm diameter Petri dishes containing 5 ml of RPMI 1640 complete medium (10% foetal calf serum, 11.2 mM glucose, 110 μg/ml sodium pyruvate and supplemented with 110 units/ml penicillin, 110 μg/ml streptomycin, and 50 μg/ml gentamycin) with or without 1.5 nM 5E3 antibody or control isotype.

Cells extraction and Mixed Lymphocytes Cultures (MLC): Human Peripheral Blood Mononuclear Cells (PBMC) were obtained by blood centrifugation for 20 min at 2000 rpm on Histopaque-1077 (SIGMA®), from healthy donors under written consent. Cells were immediately seeded with islets (see MLC section).

Mouse mesenteric lymph nodes were harvested from male C57BL/6 mice and cells were extracted by manual node structural destruction. Cells were immediately seeded with islets (see MLC section).

Aliquots of 25 IEQ were seeded with 500'000 human PBMC or mouse lymph node cells, in Millipore® Multi-screen-IP 96 wells plate, pre-coated with capture IFNγ antibody (according to manufacturer recommendations, eBiosciences® human and mouse IFNγ ELISPOT Ready-SET-Go assay kits), in a total volume of 200 μl of modified complete RPMI 1640 medium (10% foetal calf or human serum, 11.2 mM glucose, 110 μg/ml sodium pyruvate and supplemented with 110 units/ml penicillin, 110 μg/ml streptomycin, 0.5 mM β-mercaptoethanol and MEM non essential amino acid solution 1× (SIGMA®)), with or without anti-TLR4 antibodies or control isotypes. As a control, cells were seeded without islets.

After three days, cells and islets were transferred to non-adherent 96 wells plates. ELISPOT membranes were revealed according to manufacturer recommendations. Spots were counted using an automated Immunospot analyzer (Cellular Technology Ltd, Bonn, Germany).

Reaction between cells and islets was continued during four additional days before cell proliferation measurement. Cells were separated from islets by centrifugation for 1 min at 1000 rpm, fixed and permeabilized using eBioscience® Foxp3 Staining Buffer Set according to manufacturer recommendations. Following 30 minutes of incubation, cells were labelled with FITC anti-Ki-67 antibody. Cells were acquired and analyzed with a FACSCalibur flow cytometer (BDBiosciences®).

Islet transplantation: Streptozotocin (200 mg/kg i.p.) was used to induce diabetes in C57BL/6 mice at least 5 days before islet transplantation. Diabetes was defined as nonfasting blood glucose levels ≥18.0 mM for two or more consecutive days before transplantation. After overnight culture, 600 DBA1 mouse islet equivalents were transplanted under the left kidney capsule of diabetic mice. Blood sugar was monitored twice a week and mice were injected twice a week intraperitoneally with 500 μg of 5E3, control isotype or buffer (PBS), from day 0 to 28 after transplantation. Graft rejection was defined as three consecutive blood glycaemias upper than 18 mM.

Presentation of data and statistical analysis: Data are presented as mean±S.E. for "n" independent experiments, and levels of significance for differences between groups were assessed by Student's t test for unpaired groups or Log-rank (Mantel-Cox) test using GraphPad PRISM software (*=$p<0.05$, =$p<0.01$, *=$p<0.001$, ****=$p<0.0001$).

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of prolonging survival of transplanted biological material in a subject, the method comprising:
   (i) contacting the biological material to be transplanted with an antibody or immunologically active fragment thereof that specifically binds a Toll-like receptor 4 (TLR4) polypeptide to produce a transplantable composition;
   (ii) implanting the transplantable composition at a desired location in the subject; and
   (iii) administering to the subject one or more additional doses of an antibody or immunologically active fragment thereof that specifically binds TLR4, wherein the antibody is administered in an amount sufficient to prolong survival of the transplanted biological material in the subject,
   wherein the antibody or immunologically active fragment thereof that binds TLR4 in step (i), the antibody or immunologically active fragment thereof that binds TLR4 in step (iii) or the antibody or immunologically active fragment thereof that binds TLR4 in step (i) and in step (iii) comprises the heavy chain amino acid sequence MGWSWIFLFLLSGTAGVHCQVQLQESGPG LVKPSDTLSLTCAVSGYSITGGYSWH-WIRQPPGKGLEWMGYIHYSGYTDFNPSLKTRITI SRDTSKNQFSLKLSSVTAVDTAVYY-CARKDPSDAFPYWGQGTLVTVSSAST-KGPSVFPL APSSKSTSGGTAALGCLVKDYFPEP-VTVSWNSGALTSGVHTFPAVLQSSGLYSLSSVV-TV PSSSLGTQTYICNVNHKPSNTKVDKRVE-PKSCDKTHTCPPCPAPELLGGPSVFLFPPKPKD TLMISRTPEVTCVVVDVSHEDPEVKFNW-YVDGVEVHNAKTKPREEQYNSTYRVVSVLT VLHQDWLNGKEYKCKVSSKAFPAPIEK-TISKAKGQPREPQVYTLPPSREEMTKNQVSLT CLVKGFYPSDIAVEWESNGQPENNYKT-TPPVLDSDGSFFLYSKLTVDKSRWQQGNVFSC SVMHEALHNHYTQKSLSLSPGK (SEQ ID NO: 9) and the light chain amino acid sequence MEWSWV-FLFFLSVTTGVHSEIVLTQSPDFQSVTP-KEKVTITCRASQSISDHLHWYQQKPD QSPKL-LIKYASHAISGVPSRFSGSGSGTDFTLTINSLEAE-DAATYYCQQGHSFPLTFGGGT KVEIKRTVAAPS-VFIFPPSDEQLKSGTASVVCLLNN-FYPREAKVQWKVDNALQSGNSQES VTEQD-SKDSTYSLSSTLTLSKADYEKHKVYACEVTHQG-LSSPVTKSFNRGEC (SEQ ID NO: 10).

2. The method of claim 1, wherein the subject is a human.

3. The method of claim 1, wherein the biological material to be transplanted is one or more cells or cell types, one or more tissues or tissue types, or an organ or portion thereof.

4. The method of claim 1, wherein the biological material to be transplanted is allogeneic biological material.

5. The method of claim 1, wherein the biological material to be transplanted is islet cells.

6. The method of claim 5, wherein the islet cells are allogeneic islet cells.

7. The method of claim 1, wherein the biological material to be transplanted is or is derived from kidney, pancreas, liver, or intestine.

8. The method of claim 1, where the antibody or immunologically active fragment thereof that specifically binds TLR4 in steps (i) and (iii) are the same antibody or immunologically active fragment.

9. The method of claim 1, where the antibody or immunologically active fragment thereof that specifically binds TLR4 in step (i) and the antibody or immunologically active fragment thereof that specifically binds TLR4 in step (iii) are different antibodies or immunologically active fragments.

10. The method of claim 1, wherein the antibody or immunologically active fragment thereof that binds TLR4 is a full-length fully human monoclonal antibody, a $F_{ab}$ fragment, a $F_{ab'}$ fragment or a $F_{(ab')2}$ fragment, or an scFv fragment.

11. The method of claim 1, wherein the antibody or immunologically active fragment thereof that specifically binds TLR4 is administered in step (iii) in combination with one or more additional agents.

12. The method of claim 11, wherein the one or more additional agents is one or more immunosuppressive agents.

13. The method of claim 11, wherein the one or more additional agents is selected from methotrexate, cyclosporin A, tacrolimus, sirolimus, everolimus, a corticosteroid, anti-thymocyte globulin, Infliximab, Etanercept and Adalimumab.

\* \* \* \* \*

SEQUENCE LISTING

```
<160> NUMBER OF SEQ ID NOS: 47

<210> SEQ ID NO 1
<211> LENGTH: 6
<212> TYPE: PRT
<213> ORGANISM: Homo sapiens

<400> SEQUENCE: 1

Gly Gly Tyr Ser Trp His
1               5

<210> SEQ ID NO 2
<211> LENGTH: 16
<212> TYPE: PRT
<213> ORGANISM: Homo sapiens

<400> SEQUENCE: 2

Tyr Ile His Tyr Ser Gly Tyr Thr Asp Phe Asn Pro Ser Leu Lys Thr
1               5                   10                  15

<210> SEQ ID NO 3
<211> LENGTH: 9
<212> TYPE: PRT
<213> ORGANISM: Homo sapiens
```

```
<400> SEQUENCE: 3

Lys Asp Pro Ser Asp Ala Phe Pro Tyr
1               5

<210> SEQ ID NO 4
<211> LENGTH: 11
<212> TYPE: PRT
<213> ORGANISM: Homo sapiens

<400> SEQUENCE: 4

Arg Ala Ser Gln Ser Ile Ser Asp His Leu His
1               5                   10

<210> SEQ ID NO 5
<211> LENGTH: 7
<212> TYPE: PRT
<213> ORGANISM: Homo sapiens

<400> SEQUENCE: 5

Tyr Ala Ser His Ala Ile Ser
1               5

<210> SEQ ID NO 6
<211> LENGTH: 9
<212> TYPE: PRT
<213> ORGANISM: Homo sapiens

<400> SEQUENCE: 6

Gln Gln Gly His Ser Phe Pro Leu Thr
1               5

<210> SEQ ID NO 7
<211> LENGTH: 118
<212> TYPE: PRT
<213> ORGANISM: Homo sapiens

<400> SEQUENCE: 7

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Pro Ser Asp Ala Phe Pro Tyr Trp Gly Gln Gly Thr
            100                 105                 110

Leu Val Thr Val Ser Ser
        115

<210> SEQ ID NO 8
<211> LENGTH: 107
<212> TYPE: PRT
<213> ORGANISM: Homo sapiens

<400> SEQUENCE: 8

Glu Ile Val Leu Thr Gln Ser Pro Asp Phe Gln Ser Val Thr Pro Lys
1               5                   10                  15
```

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly His Ser Phe Pro Leu
                85                  90                  95

Thr Phe Gly Gly Gly Thr Lys Val Glu Ile Lys
            100                 105

<210> SEQ ID NO 9
<211> LENGTH: 467
<212> TYPE: PRT
<213> ORGANISM: Homo sapiens

<400> SEQUENCE: 9

Met Gly Trp Ser Trp Ile Phe Leu Phe Leu Leu Ser Gly Thr Ala Gly
1               5                   10                  15

Val His Cys Gln Val Gln Leu Gln Glu Ser Gly Pro Gly Leu Val Lys
            20                  25                  30

Pro Ser Asp Thr Leu Ser Leu Thr Cys Ala Val Ser Gly Tyr Ser Ile
        35                  40                  45

Thr Gly Gly Tyr Ser Trp His Trp Ile Arg Gln Pro Pro Gly Lys Gly
    50                  55                  60

Leu Glu Trp Met Gly Tyr Ile His Tyr Ser Gly Tyr Thr Asp Phe Asn
65                  70                  75                  80

Pro Ser Leu Lys Thr Arg Ile Thr Ile Ser Arg Asp Thr Ser Lys Asn
                85                  90                  95

Gln Phe Ser Leu Lys Leu Ser Ser Val Thr Ala Val Asp Thr Ala Val
            100                 105                 110

Tyr Tyr Cys Ala Arg Lys Asp Pro Ser Asp Ala Phe Pro Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

```
Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Ser Lys Ala Phe Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Lys
465

<210> SEQ ID NO 10
<211> LENGTH: 233
<212> TYPE: PRT
<213> ORGANISM: Homo sapiens

<400> SEQUENCE: 10

Met Glu Trp Ser Trp Val Phe Leu Phe Phe Leu Ser Val Thr Thr Gly
1               5                   10                  15

Val His Ser Glu Ile Val Leu Thr Gln Ser Pro Asp Phe Gln Ser Val
            20                  25                  30

Thr Pro Lys Glu Lys Val Thr Ile Thr Cys Arg Ala Ser Gln Ser Ile
        35                  40                  45

Ser Asp His Leu His Trp Tyr Gln Gln Lys Pro Asp Gln Ser Pro Lys
    50                  55                  60

Leu Leu Ile Lys Tyr Ala Ser His Ala Ile Ser Gly Val Pro Ser Arg
65                  70                  75                  80

Phe Ser Gly Ser Gly Ser Gly Thr Asp Phe Thr Leu Thr Ile Asn Ser
                85                  90                  95

Leu Glu Ala Glu Asp Ala Ala Thr Tyr Tyr Cys Gln Gln Gly His Ser
            100                 105                 110

Phe Pro Leu Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190
```

-continued

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
210                 215                 220

Thr Lys Ser Phe Asn Arg Gly Glu Cys
225                 230

<210> SEQ ID NO 11
<211> LENGTH: 839
<212> TYPE: PRT
<213> ORGANISM: Homo sapiens

<400> SEQUENCE: 11

Met Met Ser Ala Ser Arg Leu Ala Gly Thr Leu Ile Pro Ala Met Ala
1               5                   10                  15

Phe Leu Ser Cys Val Arg Pro Glu Ser Trp Glu Pro Cys Val Glu Val
                20                  25                  30

Val Pro Asn Ile Thr Tyr Gln Cys Met Glu Leu Asn Phe Tyr Lys Ile
            35                  40                  45

Pro Asp Asn Leu Pro Phe Ser Thr Lys Asn Leu Asp Leu Ser Phe Asn
        50                  55                  60

Pro Leu Arg His Leu Gly Ser Tyr Ser Phe Ser Phe Pro Glu Leu
65                  70                  75                  80

Gln Val Leu Asp Leu Ser Arg Cys Glu Ile Gln Thr Ile Glu Asp Gly
                85                  90                  95

Ala Tyr Gln Ser Leu Ser His Leu Ser Thr Leu Ile Leu Thr Gly Asn
            100                 105                 110

Pro Ile Gln Ser Leu Ala Leu Gly Ala Phe Ser Gly Leu Ser Ser Leu
        115                 120                 125

Gln Lys Leu Val Ala Val Glu Thr Asn Leu Ala Ser Leu Glu Asn Phe
130                 135                 140

Pro Ile Gly His Leu Lys Thr Leu Lys Glu Leu Asn Val Ala His Asn
145                 150                 155                 160

Leu Ile Gln Ser Phe Lys Leu Pro Glu Tyr Phe Ser Asn Leu Thr Asn
                165                 170                 175

Leu Glu His Leu Asp Leu Ser Ser Asn Lys Ile Gln Ser Ile Tyr Cys
            180                 185                 190

Thr Asp Leu Arg Val Leu His Gln Met Pro Leu Leu Asn Leu Ser Leu
        195                 200                 205

Asp Leu Ser Leu Asn Pro Met Asn Phe Ile Gln Pro Gly Ala Phe Lys
210                 215                 220

Glu Ile Arg Leu His Lys Leu Thr Leu Arg Asn Asn Phe Asp Ser Leu
225                 230                 235                 240

Asn Val Met Lys Thr Cys Ile Gln Gly Leu Ala Gly Leu Glu Val His
                245                 250                 255

Arg Leu Val Leu Gly Glu Phe Arg Asn Glu Gly Asn Leu Glu Lys Phe
            260                 265                 270

Asp Lys Ser Ala Leu Glu Gly Leu Cys Asn Leu Thr Ile Glu Glu Phe
        275                 280                 285

Arg Leu Ala Tyr Leu Asp Tyr Tyr Leu Asp Asp Ile Ile Asp Leu Phe
290                 295                 300

Asn Cys Leu Thr Asn Val Ser Ser Phe Ser Leu Val Ser Val Thr Ile
305                 310                 315                 320

Glu Arg Val Lys Asp Phe Ser Tyr Asn Phe Gly Trp Gln His Leu Glu
                325                 330                 335

```
Leu Val Asn Cys Lys Phe Gly Gln Phe Pro Thr Leu Lys Leu Lys Ser
            340                 345                 350

Leu Lys Arg Leu Thr Phe Thr Ser Asn Lys Gly Gly Asn Ala Phe Ser
            355                 360                 365

Glu Val Asp Leu Pro Ser Leu Glu Phe Leu Asp Leu Ser Arg Asn Gly
370                 375                 380

Leu Ser Phe Lys Gly Cys Cys Ser Gln Ser Asp Phe Gly Thr Thr Ser
385                 390                 395                 400

Leu Lys Tyr Leu Asp Leu Ser Phe Asn Gly Val Ile Thr Met Ser Ser
            405                 410                 415

Asn Phe Leu Gly Leu Glu Gln Leu Glu His Leu Asp Phe Gln His Ser
            420                 425                 430

Asn Leu Lys Gln Met Ser Glu Phe Ser Val Phe Leu Ser Leu Arg Asn
            435                 440                 445

Leu Ile Tyr Leu Asp Ile Ser His Thr His Thr Arg Val Ala Phe Asn
450                 455                 460

Gly Ile Phe Asn Gly Leu Ser Ser Leu Glu Val Leu Lys Met Ala Gly
465                 470                 475                 480

Asn Ser Phe Gln Glu Asn Phe Leu Pro Asp Ile Phe Thr Glu Leu Arg
            485                 490                 495

Asn Leu Thr Phe Leu Asp Leu Ser Gln Cys Gln Leu Glu Gln Leu Ser
            500                 505                 510

Pro Thr Ala Phe Asn Ser Leu Ser Ser Leu Gln Val Leu Asn Met Ser
            515                 520                 525

His Asn Asn Phe Phe Ser Leu Asp Thr Phe Pro Tyr Lys Cys Leu Asn
            530                 535                 540

Ser Leu Gln Val Leu Asp Tyr Ser Leu Asn His Ile Met Thr Ser Lys
545                 550                 555                 560

Lys Gln Glu Leu Gln His Phe Pro Ser Ser Leu Ala Phe Leu Asn Leu
            565                 570                 575

Thr Gln Asn Asp Phe Ala Cys Thr Cys Glu His Gln Ser Phe Leu Gln
            580                 585                 590

Trp Ile Lys Asp Gln Arg Gln Leu Leu Val Glu Val Glu Arg Met Glu
            595                 600                 605

Cys Ala Thr Pro Ser Asp Lys Gln Gly Met Pro Val Leu Ser Leu Asn
610                 615                 620

Ile Thr Cys Gln Met Asn Lys Thr Ile Ile Gly Val Ser Val Leu Ser
625                 630                 635                 640

Val Leu Val Val Ser Val Val Ala Val Leu Val Tyr Lys Phe Tyr Phe
            645                 650                 655

His Leu Met Leu Leu Ala Gly Cys Ile Lys Tyr Gly Arg Gly Glu Asn
            660                 665                 670

Ile Tyr Asp Ala Phe Val Ile Tyr Ser Ser Gln Asp Glu Asp Trp Val
            675                 680                 685

Arg Asn Glu Leu Val Lys Asn Leu Glu Glu Gly Val Pro Pro Phe Gln
690                 695                 700

Leu Cys Leu His Tyr Arg Asp Phe Ile Pro Gly Val Ala Ile Ala Ala
705                 710                 715                 720

Asn Ile Ile His Glu Gly Phe His Lys Ser Arg Lys Val Ile Val Val
            725                 730                 735

Val Ser Gln His Phe Ile Gln Ser Arg Trp Cys Ile Phe Glu Tyr Glu
            740                 745                 750

Ile Ala Gln Thr Trp Gln Phe Leu Ser Ser Arg Ala Gly Ile Ile Phe
```

```
                    755                 760                 765
Ile Val Leu Gln Lys Val Glu Lys Thr Leu Leu Arg Gln Gln Val Glu
770                 775                 780

Leu Tyr Arg Leu Leu Ser Arg Asn Thr Tyr Leu Glu Trp Glu Asp Ser
785                 790                 795                 800

Val Leu Gly Arg His Ile Phe Trp Arg Arg Leu Arg Lys Ala Leu Leu
                805                 810                 815

Asp Gly Lys Ser Trp Asn Pro Glu Gly Thr Val Gly Thr Gly Cys Asn
                820                 825                 830

Trp Gln Glu Ala Thr Ser Ile
                835

<210> SEQ ID NO 12
<211> LENGTH: 1404
<212> TYPE: DNA
<213> ORGANISM: Homo sapiens

<400> SEQUENCE: 12
atgggatgga gctggatctt tctcttcctc ctgtcaggaa ctgcaggtgt acattgccag    60
gtgcagcttc aggagtccgg cccaggactg gtgaagcctt cggacaccct gtccctcacc   120
tgcgctgtct ctggttactc catcaccggt ggttatagct ggcactggat acggcagccc   180
ccagggaagg gactgagtg gatggggtat atccactaca gtggttacac tgacttcaac   240
ccctccctca gactcgaat caccatatca cgtgacacgt ccaagaacca gttctccctg   300
aagctgagct ctgtgaccgc tgtggacact gcagtgtatt actgtgcgag aaaagatccg   360
tccgacgcct ttccttactg gggccaaggg actctggtca ctgtctcttc cgcctccacc   420
aagggcccat cggtcttccc cctggcaccc tcctccaaga gcacctctgg ggcacagcg    480 gccctgggct gcctggtcaa ggactacttc cccgaaccgg tgacggtgtc gtggaactca   540
ggcgccctga ccagcggcgt gcacaccttc cggctgtcc tacagtcctc aggactctac    600
tccctcagca gcgtggtgac cgtgccctcc agcagcttgg gcacccagac ctacatctgc   660
aacgtgaatc acaagcccag caacaccaag gtggacaaga gagttgagcc caaatcttgt   720
gacaaaactc acacatgccc accgtgccca gcacctgaac tcctgggggg accgtcagtc   780
ttcctcttcc ccccaaaacc caaggacacc ctcatgatct cccggacccc tgaggtcaca   840
tgcgtggtgg tggacgtgag ccacgaagac cctgaggtca agttcaactg gtacgtggac   900
ggcgtggagg tgcataatgc caagacaaag ccgcgggagg agcagtacaa cagcacgtac   960
cgtgtggtca gcgtcctcac cgtcctgcac caggactggc tgaatggcaa ggagtacaaa  1020
tgcaaggtct ccagtaaagc ctttcctgcc cccatcgaga aaaccatctc caaagccaaa  1080
gggcagcccc gagaaccaca ggtgtacacc ctgcccccat cccgggagga gatgaccaag  1140
aaccaggtca gcctgacctg cctggtcaaa ggcttctatc ccagcgacat cgccgtggag  1200
tgggagagca atgggcagcc ggagaacaac tacaagacca cgcctcccgt gctggactcc  1260
gacggctcct tcttcctcta tagcaagctc accgtggaca agagcaggtg gcagcagggg  1320
aacgtcttct catgctccgt gatgcatgag gctctgcaca accactacac gcagaagagc  1380
ctctccctgt ctccgggtaa atag                                         1404

<210> SEQ ID NO 13
<211> LENGTH: 702
<212> TYPE: DNA
<213> ORGANISM: Homo sapiens

<400> SEQUENCE: 13
```

-continued

```
atggaatgga gctgggtctt tctcttcttc ctgtcagtaa ctacaggtgt ccactccgaa      60
attgtgttga cgcagtctcc agactttcag tctgtgactc caaaggaaaa agtcaccatc     120
acctgcaggg ccagtcagag tatcagcgac cacttacact ggtaccaaca gaaacctgat    180
cagtctccca agctcctcat caaatatgct tcccatgcca tttctggggt cccatcgagg    240
ttcagtggca gtgggtctgg gacagacttc actctcacca tcaatagcct agaggctgaa    300
gatgctgcaa cgtattactg tcagcagggt cacagttttc cgctcacttt cggcggaggg    360
accaaggtgg agatcaaacg tacggtggct gcaccatctg tcttcatctt cccgccatct    420
gatgagcagt tgaaatctgg aactgcctct gttgtgtgcc tgctgaataa cttctatccc    480
agagaggcca agtacagtg aaggtggat aacgccctcc aatcgggtaa ctcccaggag     540
agtgtcacag agcaggacag caaggacagc acctacagcc tcagcagcac cctgacgctg    600
agcaaagcag actacgagaa acacaaagtc tacgcctgcg aagtcaccca tcagggcctg    660
agctcgcccg tcacaaagag cttcaacagg ggagagtgtt ag                       702
```

<210> SEQ ID NO 14
<211> LENGTH: 118
<212> TYPE: PRT
<213> ORGANISM: Homo sapiens
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid

<400> SEQUENCE: 14

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Xaa Gly Gly
            20                  25                  30

Tyr Ser Trp His Trp Ile Arg Gln Pro Pro Gly Lys Gly Leu Glu Trp
        35                  40                  45

Xaa Gly Tyr Ile His Tyr Ser Gly Tyr Thr Asp Phe Asn Pro Ser Leu
    50                  55                  60

Lys Thr Arg Xaa Thr Xaa Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Pro Ser Asp Gly Phe Pro Tyr Trp Gly Gln Gly Thr
            100                 105                 110

Leu Val Thr Val Ser Ser
        115

<210> SEQ ID NO 15
<211> LENGTH: 118
<212> TYPE: PRT
<213> ORGANISM: Homo sapiens
<220> FEATURE:
<221> NAME/KEY: misc_feature

```
<222> LOCATION: (24)..(24)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Xaa Ser Gly Tyr Ser Ile Thr Gly Gly
            20                  25                  30

Tyr Ser Trp His Trp Val Arg Gln Ala Pro Gly Lys Gly Leu Glu Trp
        35                  40                  45

Xaa Ser Tyr Ile His Tyr Ser Gly Tyr Thr Asp Phe Asn Pro Ser Leu
50                  55                  60

Lys Thr Arg Phe Thr Ile Ser Arg Asp Asn Ser Lys Asn Thr Xaa Tyr
65                  70                  75                  80

Leu Gln Met Asn Ser Leu Arg Ala Glu Asp Thr Ala Val Tyr Tyr Cys
                85                  90                  95

Ala Arg Lys Asp Pro Ser Asp Gly Phe Pro Tyr Trp Gly Gln Gly Thr
            100                 105                 110

Leu Val Thr Val Ser Ser
            115

<210> SEQ ID NO 16
<211> LENGTH: 107
<212> TYPE: PRT
<213> ORGANISM: Homo sapiens
<220> FEATURE:
<221> NAME/KEY: misc_feature
<222> LOCATION: (49)..(49)
<223> OTHER INFORMATION: Xaa can be any naturally occurring amino acid

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asp His
            20                  25                  30

Leu His Trp Tyr Gln Gln Lys Pro Gly Gln Ala Pro Arg Leu Leu Ile
        35                  40                  45

Xaa Tyr Ala Ser His Ala Ile Ser Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gly Gly Thr Lys Val Glu Ile Lys
            100                 105

<210> SEQ ID NO 17
<211> LENGTH: 9
<212> TYPE: PRT
<213> ORGANISM: Homo sapiens

<400> SEQUENCE: 17

Gln Asn Gly His Ser Phe Pro Leu Thr
1               5
```

<210> SEQ ID NO 18
<211> LENGTH: 107
<212> TYPE: PRT
<213> ORGANISM: Homo sapiens

<400> SEQUENCE: 18

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Asn Gly His Ser Phe Pro Leu
                85                  90                  95

Thr Phe Gly Gly Gly Thr Lys Val Glu Ile Lys
            100                 105
```

<210> SEQ ID NO 19
<211> LENGTH: 120
<212> TYPE: PRT
<213> ORGANISM: Homo sapiens
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid

<400> SEQUENCE: 19

```
Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Ser
            20                  25                  30

Tyr Ile His Trp Val Arg Gln Ala Pro Gly Gln Gly Leu Glu Trp Xaa
        35                  40                  45

Gly Trp Thr Asp Pro Glu Asn Val Asn Ser Ile Tyr Asp Pro Arg Phe
    50                  55                  60

Gln Gly Arg Val Thr Ile Thr Ala Asp Xaa Ser Thr Ser Thr Ala Tyr
65                  70                  75                  80

Xaa Glu Leu Ser Ser Leu Arg Ser Glu Asp Thr Ala Val Tyr Tyr Cys
                85                  90                  95

Ala Arg Gly Tyr Asn Gly Val Tyr Tyr Ala Met Asp Tyr Trp Gly Gln
            100                 105                 110

Gly Thr Thr Val Thr Val Ser Ser
        115                 120
```

<210> SEQ ID NO 20
<211> LENGTH: 5
<212> TYPE: PRT
<213> ORGANISM: Homo sapiens

-continued

```
<400> SEQUENCE: 20

Asp Ser Tyr Ile His
1               5

<210> SEQ ID NO 21
<211> LENGTH: 17
<212> TYPE: PRT
<213> ORGANISM: Homo sapiens

<400> SEQUENCE: 21

Trp Thr Asp Pro Glu Asn Val Asn Ser Ile Tyr Asp Pro Arg Phe Gln
1               5                   10                  15

Gly

<210> SEQ ID NO 22
<211> LENGTH: 11
<212> TYPE: PRT
<213> ORGANISM: Homo sapiens

<400> SEQUENCE: 22

Gly Tyr Asn Gly Val Tyr Tyr Ala Met Asp Tyr
1               5                   10

<210> SEQ ID NO 23
<211> LENGTH: 106
<212> TYPE: PRT
<213> ORGANISM: Homo sapiens
<220> FEATURE:
<221> NAME/KEY: misc_feature
<222> LOCATION: (70)..(70)
<223> OTHER INFORMATION: Xaa can be any naturally occurring amino acid

<400> SEQUENCE: 23

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Val Ile Tyr Met
                20                  25                  30

His Trp Tyr Gln Gln Lys Pro Gly Gln Ala Pro Arg Leu Leu Ile Tyr
            35                  40                  45

Arg Thr Tyr Asn Leu Ala Ser Gly Ile Pro Ala Arg Phe Ser Gly Ser
        50                  55                  60

Gly Ser Gly Thr Asp Xaa Thr Leu Thr Ile Ser Ser Leu Glu Pro Glu
65                  70                  75                  80

Asp Phe Ala Val Tyr Tyr Cys His Gln Trp Ser Ser Phe Pro Tyr Thr
                85                  90                  95

Phe Gly Gln Gly Thr Lys Val Glu Ile Lys
            100                 105

<210> SEQ ID NO 24
<211> LENGTH: 10
<212> TYPE: PRT
<213> ORGANISM: Homo sapiens

<400> SEQUENCE: 24

Ser Ala Ser Ser Ser Val Ile Tyr Met His
1               5                   10

<210> SEQ ID NO 25
<211> LENGTH: 7
<212> TYPE: PRT
<213> ORGANISM: Homo sapiens

<400> SEQUENCE: 25
```

Arg Thr Tyr Asn Leu Ala Ser
1               5

<210> SEQ ID NO 26
<211> LENGTH: 9
<212> TYPE: PRT
<213> ORGANISM: Homo sapiens

<400> SEQUENCE: 26

His Gln Trp Ser Ser Phe Pro Tyr Thr
1               5

<210> SEQ ID NO 27
<211> LENGTH: 121
<212> TYPE: PRT
<213> ORGANISM: Homo sapiens
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid

<400> SEQUENCE: 27

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Xaa Thr Tyr
            20                  25                  30

Asn Ile Gly Val Gly Trp Ile Arg Gln Pro Pro Gly Lys Ala Leu Glu
        35                  40                  45

Trp Leu Ala His Ile Trp Trp Asn Asp Asn Ile Tyr Tyr Asn Thr Val
    50                  55                  60

Leu Lys Ser Arg Leu Thr Xaa Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Xaa Arg Met Ala Glu Gly Arg Tyr Asp Ala Met Asp Tyr Trp Gly
            100                 105                 110

Gln Gly Thr Leu Val Thr Val Ser Ser
        115                 120

<210> SEQ ID NO 28
<211> LENGTH: 7
<212> TYPE: PRT
<213> ORGANISM: Homo sapiens

<400> SEQUENCE: 28

Thr Tyr Asn Ile Gly Val Gly
1               5

<210> SEQ ID NO 29
<211> LENGTH: 16
<212> TYPE: PRT
<213> ORGANISM: Homo sapiens

<400> SEQUENCE: 29

His Ile Trp Trp Asn Asp Asn Ile Tyr Tyr Asn Thr Val Leu Lys Ser
1               5                   10                  15

```
<210> SEQ ID NO 30
<211> LENGTH: 11
<212> TYPE: PRT
<213> ORGANISM: Homo sapiens

<400> SEQUENCE: 30

Met Ala Glu Gly Arg Tyr Asp Ala Met Asp Tyr
1               5                   10

<210> SEQ ID NO 31
<211> LENGTH: 121
<212> TYPE: PRT
<213> ORGANISM: Homo sapiens
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Xaa Ser Gly Phe Ser Leu Thr Thr Tyr
            20                  25                  30

Asn Ile Gly Val Gly Trp Val Arg Gln Ala Pro Gly Lys Gly Leu Glu
        35                  40                  45

Trp Xaa Ser His Ile Trp Trp Asn Asp Asn Ile Tyr Tyr Asn Thr Val
    50                  55                  60

Leu Lys Ser Arg Leu Thr Xaa Ser Xaa Asp Asn Ser Lys Asn Thr Xaa
65                  70                  75                  80

Tyr Leu Gln Met Asn Ser Leu Arg Ala Glu Asp Thr Ala Val Tyr Tyr
                85                  90                  95

Cys Xaa Arg Met Ala Glu Gly Arg Tyr Asp Ala Met Asp Tyr Trp Gly
            100                 105                 110

Gln Gly Thr Leu Val Thr Val Ser Ser
        115                 120

<210> SEQ ID NO 32
<211> LENGTH: 107
<212> TYPE: PRT
<213> ORGANISM: Homo sapiens
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (87)..(87)
```

<223> OTHER INFORMATION: Xaa can be any naturally occurring amino acid

<400> SEQUENCE: 32

```
Asp Ile Gln Met Thr Gln Ser Pro Ser Ser Val Ser Ala Ser Val Gly
 1               5                  10                  15
Asp Arg Val Thr Ile Thr Cys Arg Ala Ser Gln Asp Ile Thr Asn Tyr
                20                  25                  30
Leu Asn Trp Tyr Gln Gln Lys Pro Gly Lys Ala Pro Lys Leu Leu Ile
            35                  40                  45
Tyr Tyr Thr Ser Lys Leu His Ser Gly Val Pro Ser Arg Phe Ser Gly
 50                  55                  60
Ser Gly Ser Gly Thr Asp Xaa Thr Leu Thr Ile Ser Ser Leu Gln Pro
 65                  70                  75                  80
Glu Asp Phe Ala Thr Tyr Xaa Cys Gln Gln Gly Asn Thr Phe Pro Trp
                85                  90                  95
Thr Phe Gly Gly Gly Thr Lys Val Glu Ile Lys
            100                 105
```

<210> SEQ ID NO 33
<211> LENGTH: 11
<212> TYPE: PRT
<213> ORGANISM: Homo sapiens

<400> SEQUENCE: 33

```
Arg Ala Ser Gln Asp Ile Thr Asn Tyr Leu Asn
 1               5                  10
```

<210> SEQ ID NO 34
<211> LENGTH: 7
<212> TYPE: PRT
<213> ORGANISM: Homo sapiens

<400> SEQUENCE: 34

```
Tyr Thr Ser Lys Leu His Ser
 1               5
```

<210> SEQ ID NO 35
<211> LENGTH: 9
<212> TYPE: PRT
<213> ORGANISM: Homo sapiens

<400> SEQUENCE: 35

```
Gln Gln Gly Asn Thr Phe Pro Trp Thr
 1               5
```

<210> SEQ ID NO 36
<211> LENGTH: 118
<212> TYPE: PRT
<213> ORGANISM: Homo sapiens

<400> SEQUENCE: 36

```
Gln Val Gln Leu Gln Glu Ser Gly Pro Gly Leu Val Lys Pro Ser Asp
 1               5                  10                  15
Thr Leu Ser Leu Thr Cys Ala Val Ser Gly Tyr Ser Ile Thr Gly Gly
                20                  25                  30
Tyr Ser Trp His Trp Ile Arg Gln Pro Pro Gly Lys Gly Leu Glu Trp
            35                  40                  45
Met Gly Tyr Ile His Tyr Ser Gly Tyr Thr Asp Phe Asn Pro Ser Leu
 50                  55                  60
Lys Thr Arg Ile Thr Ile Ser Arg Asp Thr Ser Lys Asn Gln Phe Ser
 65                  70                  75                  80
```

```
Leu Lys Leu Ser Ser Val Thr Ala Val Asp Thr Ala Val Tyr Tyr Cys
                85                  90                  95

Ala Arg Lys Asp Pro Ser Asp Ala Phe Pro Tyr Trp Gly Gln Gly Thr
            100                 105                 110

Leu Val Thr Val Ser Ser
        115

<210> SEQ ID NO 37
<211> LENGTH: 354
<212> TYPE: DNA
<213> ORGANISM: Homo sapiens

<400> SEQUENCE: 37
caggtgcagc ttcaggagtc cggcccagga ctggtgaagc cttcggacac cctgtccctc      60
acctgcgctg tctctggtta ctccatcacc ggtggttata ctggcactg gatacggcag     120 cccccaggga agggactgga gtggatgggg tatatccact acagtggtta cactgacttc     180 aaccccctccc tcaagactcg aatcaccata tcacgtgaca cgtccaagaa ccagttctcc    240
ctgaagctga gctctgtgac cgctgtggac actgcagtgt attactgtgc gagaaaagat    300
ccgtccgacg cctttcctta ctggggccaa gggactctgg tcactgtctc ttcc           354

<210> SEQ ID NO 38
<211> LENGTH: 118
<212> TYPE: PRT
<213> ORGANISM: Homo sapiens

<400> SEQUENCE: 38

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Pro Ser Glu Gly Phe Pro Tyr Trp Gly Gln Gly Thr
            100                 105                 110

Leu Val Thr Val Ser Ser
        115

<210> SEQ ID NO 39
<211> LENGTH: 354
<212> TYPE: DNA
<213> ORGANISM: Homo sapiens

<400> SEQUENCE: 39
caggtgcagc ttcaggagtc cggcccagga ctggtgaagc cttcggacac cctgtccctc      60
acctgcgctg tctctggtta ctccatcacc ggtggttata ctggcactg gatacggcag     120 cccccaggga agggactgga gtggatgggg tatatccact acagtggtta cactgacttc     180 aaccccctccc tcaagactcg aatcaccata tcacgtgaca cgtccaagaa ccagttctcc    240
ctgaagctga gctctgtgac cgctgtggac actgcagtgt attactgtgc gagaaaagat    300
```
ccgtccgagg gatttcctta ctggggccaa gggactctgg tcactgtctc ttcc    354

<210> SEQ ID NO 40
<211> LENGTH: 107
<212> TYPE: PRT
<213> ORGANISM: Homo sapiens

<400> SEQUENCE: 40

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Asn Ser His Ser Phe Pro Leu
                85                  90                  95

Thr Phe Gly Gly Gly Thr Lys Val Glu Ile Lys
            100                 105

<210> SEQ ID NO 41
<211> LENGTH: 321
<212> TYPE: DNA
<213> ORGANISM: Homo sapiens

<400> SEQUENCE: 41
gaaattgtgt tgacgcagtc tccagacttt cagtctgtga ctccaaagga aaaagtcacc    60
atcacctgca gggccagtca gagtatcagc gaccacttac actggtacca acagaaacct   120
gatcagtctc ccaagctcct catcaaatat gcttcccatg ccatttctgg ggtcccatcg   180
aggttcagtg gcagtgggtc tgggacagac ttcactctca ccatcaatag cctagaggct   240
gaagatgctg caacgtatta ctgtcagaat agtcacagtt ttccgctcac tttcggcgga   300
gggaccaagg tggagatcaa a                                             321

<210> SEQ ID NO 42
<211> LENGTH: 107
<212> TYPE: PRT
<213> ORGANISM: Homo sapiens

<400> SEQUENCE: 42

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly His Ser Phe Pro Leu
                85                  90                  95

Thr Phe Gly Gly Gly Thr Lys Val Glu Ile Lys
            100                 105

<210> SEQ ID NO 43
<211> LENGTH: 321
<212> TYPE: DNA
<213> ORGANISM: Homo sapiens

<400> SEQUENCE: 43
gaaattgtgt tgacgcagtc tccagacttt cagtctgtga ctccaaagga aaaagtcacc    60
atcacctgca gggccagtca gagtatcagc gaccacttac actggtacca acagaaacct   120
gatcagtctc ccaagctcct catcaaatat gcttcccatg ccatttctgg ggtcccatcg   180
aggttcagtg gcagtgggtc tgggacagac ttcactctca ccatcaatag cctagaggct   240
gaagatgctg caacgtatta ctgtcagcag ggtcacagtt ttccgctcac tttcggcgga   300
gggaccaagg tggagatcaa a                                              321

<210> SEQ ID NO 44
<211> LENGTH: 107
<212> TYPE: PRT
<213> ORGANISM: Homo sapiens

<400> SEQUENCE: 44

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Asn Ser Ser Ser Phe Pro Leu
                85                  90                  95

Thr Phe Gly Gly Gly Thr Lys Val Glu Ile Lys
            100                 105

<210> SEQ ID NO 45
<211> LENGTH: 321
<212> TYPE: DNA
<213> ORGANISM: Homo sapiens

<400> SEQUENCE: 45
gaaattgtgt tgacgcagtc tccagacttt cagtctgtga ctccaaagga aaaagtcacc    60
atcacctgca gggccagtca gagtatcagc gaccacttac actggtacca acagaaacct   120
gatcagtctc ccaagctcct catcaaatat gcttcccatg ccatttctgg ggtcccatcg   180
aggttcagtg gcagtgggtc tgggacagac ttcactctca ccatcaatag cctagaggct   240
gaagatgctg caacgtatta ctgtcagaat agtagtagtt ttccgctcac tttcggcgga   300
gggaccaagg tggagatcaa a                                              321

<210> SEQ ID NO 46
<211> LENGTH: 107
<212> TYPE: PRT
<213> ORGANISM: Homo sapiens

<400> SEQUENCE: 46

Glu Ile Val Leu Thr Gln Ser Pro Asp Phe Gln Ser Val Thr Pro Lys
1               5                   10                  15

```
Glu Lys Val Thr Ile Thr Cys Arg Ala Ser Gln Ser Ile Ser Asp His
                20              25                  30

Leu His Trp Tyr Gln Gln Lys Pro Asp Gln Ser Pro Lys Leu Leu Ile
            35              40              45

Lys Tyr Ala Ser His Ala Ile Ser Gly Val Pro Ser Arg Phe Ser Gly
        50              55              60

Ser Gly Ser Gly Thr Asp Phe Thr Leu Thr Ile Asn Ser Leu Glu Ala
65              70                  75                  80

Glu Asp Ala Ala Thr Tyr Tyr Cys Gln Gln Ser His Ser Phe Pro Leu
                85              90              95

Thr Phe Gly Gly Gly Thr Lys Val Glu Ile Lys
            100             105

<210> SEQ ID NO 47
<211> LENGTH: 321
<212> TYPE: DNA
<213> ORGANISM: Homo sapiens

<400> SEQUENCE: 47
gaaattgtgt tgacgcagtc tccagacttt cagtctgtga ctccaaagga aaaagtcacc     60
atcacctgca gggccagtca gagtatcagc gaccacttac actggtacca acagaaacct    120
gatcagtctc ccaagctcct catcaaatat gcttcccatg ccatttctgg ggtcccatcg    180
aggttcagtg gcagtgggtc tgggacagac ttcactctca ccatcaatag cctagaggct    240
gaagatgctg caacgtatta ctgtcagcag agtcacagtt ttccgctcac tttcggcgga    300
gggaccaagg tggagatcaa a                                              321
```